US008410023B2

(12) United States Patent
Slomczynska et al.

(10) Patent No.: US 8,410,023 B2
(45) Date of Patent: Apr. 2, 2013

(54) COMPOSITIONS AND METHODS FOR CONTROLLING NEMATODES

(75) Inventors: Urszula Slomczynska, Ballwin, MO (US); Matt W. Dimmic, Maryland Heights, MO (US); William P. Haakenson, Jr., St. Louis, MO (US); Al Wideman, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 12/904,724

(22) Filed: Oct. 14, 2010

(65) Prior Publication Data

US 2011/0028320 A1    Feb. 3, 2011

Related U.S. Application Data

(63) Continuation of application No. 12/703,750, filed on Feb. 10, 2010, now Pat. No. 8,017, 555.

(60) Provisional application No. 61/151,482, filed on Feb. 10, 2009.

(51) Int. Cl.
*A01N 25/00* (2006.01)
*A01N 43/836* (2006.01)
*A01N 43/76* (2006.01)
*A61K 31/4245* (2006.01)
*A61K 31/433* (2006.01)
*A61K 31/422* (2006.01)
*C07D 413/06* (2006.01)
*C07D 417/06* (2006.01)

(52) U.S. Cl. ............ 504/116.1; 514/364; 514/361; 514/374; 548/131; 548/128; 548/235

(58) Field of Classification Search ............ 504/116.1; 548/131, 128, 235; 514/364, 361, 374
See application file for complete search history.

(56) References Cited

U.S. PATENT DOCUMENTS

| 3,192,103 | A | 6/1965 | Sousa et al. |
| 3,211,742 | A | 10/1965 | Lenaers et al. |
| 3,218,331 | A | 11/1965 | Eloy et al. |
| 3,227,725 | A | 1/1966 | Eloy et al. |
| 3,264,318 | A | 8/1966 | Eloy et al. |
| 4,791,124 | A | 12/1988 | Lutomski et al. |
| 4,908,357 | A | 3/1990 | Lutomski |
| 5,633,271 | A | 5/1997 | Amoo et al. |
| 5,912,243 | A | 6/1999 | Dowling et al. |
| 5,985,904 | A | 11/1999 | Jeschke et al. |
| 6,048,714 | A | 4/2000 | Hiromoto |
| 6,310,049 | B1 | 10/2001 | Wada et al. |
| 7,041,685 | B2 | 5/2006 | Cai et al. |
| 2002/0013326 | A1 | 1/2002 | Tiebes et al. |
| 2003/0045546 | A1 | 3/2003 | Cai et al. |
| 2003/0162812 | A1 | 8/2003 | Harmsen et al. |
| 2004/0204461 | A1* | 10/2004 | Karp et al. .......... 514/364 |
| 2005/0004005 | A1 | 1/2005 | Kasibhatla et al. |
| 2009/0012031 | A1 | 1/2009 | Chinnaiyan et al. |
| 2009/0048311 | A1 | 2/2009 | Williams et al. |

FOREIGN PATENT DOCUMENTS

| WO |    9519353    | 7/1995 |
| WO | WO0035285     | 6/2000 |
| WO | WO0035913     | 6/2000 |
| WO | WO02100826    | 12/2002 |
| WO | WO2004058253  | 7/2004 |
| WO | WO2006114400  | 11/2006 |
| WO | WO2007/043400 | 4/2007 |
| WO | WO2009/100438 | 8/2009 |

OTHER PUBLICATIONS

Anon., Herbicidal oxadiazole derivatives, 1990, Research Disclosure, 317, 777-9.*
R.M. Srivastava et al., Synthesis of 3-Aryl-5-[Thien-3-yl Methyl]-1,2,4-Oxadiazoles, 1999, Synthetic Communications, 29(9), 1437-1450.*
How to Identify and Manage Pine Wilt Disease and Treat Wood Products Infested by the Pinewood Nematodes [online] retrieved from the Internet on Jun. 5, 2010. [URL:http://na.fs.fed.us/spfo/pubs/howtos/ht_pinewilt/pinewilt.htm].
Bridge, et al. *Musa* Pest Fact Sheet No. 2 Nov. 1997.
Barker et al., "Plant and Soil Nematodes: Societal Impact and Focus for the Future," *J. Nematol.*, 26(2):127-137 (1994).
Becker, "Seeking New Controls for Costly Nematodes," *Agricultural Research*, pp. 22-24 (Mar. 1999).
Carpenter et al., "Township limits on 1,3-D will impact adjustment to methyl bromide phase-out," *California Agriculture*, 55(3):12-18 (May-Jun. 2001).
Carter, "Costs Uncertain: Methyl bromide phase-out becomes reality" California Agriculture 55(3):2, 2001.
Crow, "Alternatives to Fenamiphos for Management of Plant-Parasitic Nematodes on Bermudagrass," *J. Nematol.*, 37(4):477-482 (2005).
Geerts et al., "Anthelmintic Resistance in Human Helminths: Learning from the Problems with Worm Control in Livestock" Parasitology Today 13:149-151, 1997.
Hackney et al., "Marigold, Castor Bean, and Chrysanthemum as Controls of *Meloidogyne incognita* and *Pratylenchus alleni*," *J. Nematol.*, 7(1):84-90 (1975).
Prichard, "Anthelmintic Restistance" Veterinary Parasitology 54:259-268, 1994.
Sangster et al., "Pharmacology of Anthelmintic Restistance" Parasitology Today 15(4):141-146, 1999.
Zhang et al., "Discovery and Structure-Activity Relationship of 3-Aryl-5-aryl-1 . . . " J. of Medic. Chem. 48(16):5215-5223, 2005.
Voron'Ko M N et al., "Synthesis of 3,5-disubstituted 1,2,4-oxadiazoles and reactivity of N-hydroxybenzamidines," Russian Federation 49:60-63 (2006).
Julian J Prieto et al., "Application of linear discriminant analysis in the virtual screening of antichagasic drugs through trypanothione reductase inhibition," Molecular Diversity 10:361-375 (2006).

(Continued)

Primary Examiner — Kristin Bianchi
(74) *Attorney, Agent, or Firm* — Senniger Powers LLP; Molly B. Edwards

(57) ABSTRACT

Compositions and processes for controlling nematodes are described herein, e.g., nematodes that infest plants or animals. The compounds include oxazoles, oxadiazoles and thiadiazoles.

32 Claims, No Drawings

OTHER PUBLICATIONS

Jessen K A et al., "The Discovery and Mechanism of Action of Novel Tumor-Selective and Apoptosis-Inducing 3,5-Diary-1, 2,4-Oxadiazole Series Using a Chemical Genetics Approach," Molecular Cancer Therapeutics, American Association of Cancer Research 4:761-771 (2005).

Yale H L et al., "3,5-Disubstituted-1, 2,4-Oxadiazoles and 4,5-Dihydro-3, 5-Disubstituted 1,2,4-Oxadiazoles," Journal of Heterocyclic Chemistry 15:1373-1378 (1978).

Iino Minoru et al., "Rational Design and Evaluation of New Lead Compound Structures for Selective .beta.ARK1 Inhibitors," Journal of Medicinal Chemistry, American Chemical Society 45:2150-2159 (2002).

Wang Ying et al, "Rapid and efficient synthesis of 1,2,4-oxadiazoles utilizing polymer-supported reagents under microwave heating," Organic Letters 7:925-928 (2005).

"1,2,4-Oxadiazole,5(3-chloro-2-thienyl)-3-phenoxy," Jun. 8, 2008, Database Accession No. 1026287-93-3, Database Registry, Chemical Abstracts Service, Columbus, OH, XP002696671, 1 page.

Supplemental European Search Report issued Nov. 19, 2012 in European Patent Application No. 10741639.8, 10 pages.

* cited by examiner

COMPOSITIONS AND METHODS FOR CONTROLLING NEMATODES

This application claims priority to U.S. application Ser. No. 12/703,750, which was filed on Feb. 10, 2010 now U.S. Pat. No. 8,017,555, which claims priority to U.S. Provisional No. 61/151,482, which was filed on Feb. 10, 2009.

BACKGROUND

Nematodes (derived from the Greek word for thread) are active, flexible, elongate, organisms that live on moist surfaces or in liquid environments, including films of water within soil and moist tissues within other organisms. While only 20,000 species of nematode have been identified, it is estimated that 40,000 to 10 million actually exist. Many species of nematodes have evolved to be very successful parasites of plants and animals and are responsible for significant economic losses in agriculture and livestock and for morbidity and mortality in humans (Whitehead (1998) *Plant Nematode Control*. CAB International, New York).

Nematode parasites of plants can infest all parts of plants, including roots, developing flower buds, leaves, and stems. Plant parasites are classified on the basis of their feeding habits into the broad categories migratory ectoparasites, migratory endoparasites, and sedentary endoparasites. Sedentary endoparasites, which include the root knot nematodes (*Meloidogyne*) and cyst nematodes (*Globodera* and *Heterodera*) induce feeding sites and establish long-term infections within roots that are often very damaging to crops (Whitehead, supra). It is estimated that parasitic nematodes cost the horticulture and agriculture industries in excess of $78 billion worldwide a year, based on an estimated average 12% annual loss spread across all major crops. For example, it is estimated that nematodes cause soybean losses of approximately $3.2 billion annually worldwide (Barker et al. (1994) *Plant and Soil Nematodes: Societal Impact and Focus for the Future*. The Committee on National Needs and Priorities in Nematology. Cooperative State Research Service, US Department of Agriculture and Society of Nematologists). Several factors make the need for safe and effective nematode controls urgent. Continuing population growth, famines, and environmental degradation have heightened concern for the sustainability of agriculture, and new government regulations may prevent or severely restrict the use of many available agricultural anthelmintic agents.

There are a very small array of chemicals available to effectively control nematodes (Becker (1999) *Agricultural Research Magazine* 47(3):22-24; U.S. Pat. No. 6,048,714). In general, chemical nematicides are highly toxic compounds known to cause substantial environmental damage and are increasingly restricted in the amounts and locations in which they can be used. For example, the soil fumigant methyl bromide which has been used effectively to reduce nematode infestations in a variety of specialty crops, is regulated under the U.N. Montreal Protocol as an ozone-depleting substance and is undergoing phase out in the US and world wide (Carter (2001) *California Agriculture*, 55(3):2). It is expected that strawberry and other commodity crop industries will be significantly impacted if a suitable replacement for methyl bromide is not found. Similarly, broad-spectrum nematicides such as Telone (various formulations of 1,3-dichloropropene) have significant restrictions on their use because of toxicological concerns (Carter (2001) *California Agriculture*, 55(3):12-18). Organophosphate and carbamate pesticides are another important class of nematicides undergoing regulatory review and several of these compounds are currently being phase out (e.g., fenamiphos, terbufos, cadusafos).

To date little success has been achieved in finding safe effective replacements for the toxic but efficacious conventional nematicides. A recent example of the poor efficacy of many newer potential replacements for organophosphates and carbamates is the study of alternatives to fenamiphos for management of plant parasitic nematodes in bermudagrass. In these trials, none of the experimental treatments reduced population densities of the plant parasitic nematodes, or consistently promoted turf visual performance or turf root production (Crow (2005) *Journal of Nematology*, 37(4):477-482). Consequently there remains an urgent need to develop environmentally safe, efficacious methods of controlling plant parasitic nematodes Some plant species are known to be highly resistant to nematodes. The best documented of these include marigolds (*Tagetes* spp.), rattlebox (*Crotalaria spectabilis*), chrysanthemums (*Chrysanthemum* spp.), castor bean (*Ricinus communis*), margosa (*Azardiracta indica*), and many members of the family Asteraceae (family Compositae) (Hackney & Dickerson. (1975) *J Nematol* 7(1):84-90). In the case of the Asteraceae, the photodynamic compound alpha-terthienyl has been shown to account for the strong nematicidal activity of the roots. Castor beans are plowed under as a green manure before a seed crop is set. However, a significant drawback of the castor plant is that the seed contains toxic compounds (such as ricin) that can kill humans, pets, and livestock and is also highly allergenic. In most cases however, the active principle(s) for plant nematicidal activity has not been discovered and it remains difficult to derive commercially successful nematicidal products from these resistant plants or to transfer the resistance to crops of agronomical importance such as soybeans and cotton.

Genetic resistance to certain nematodes is available in some commercial cultivars (e.g., soybeans), but these are restricted in number and the availability of cultivars with both desirable agronomic features and resistance is limited. Furthermore, the production of nematode resistant commercial varieties by conventional plant breeding based on genetic recombination through sexual crosses is a slow process and is often further hampered by a lack of appropriate germplasm.

Chemical means of controlling plant parasitic nematodes continue to be essential for many crops which lack adequate natural resistance or a source of transgenic resistance. In the specialty markets, economic hardship resulting from nematode infestation is particularly high in strawberries, bananas, and other high value vegetables and fruits. In the high-acreage crop markets, nematode damage is greatest in soybeans and cotton. There are however, dozens of additional crops that suffer from significant nematode infestation including potato, pepper, onion, citrus, coffee, sugarcane, greenhouse ornamentals and golf course turf grasses.

To be useful in modern agriculture nematicides must have high potency, a broad spectrum of activity against different strains of nematodes and should not be toxic to non-target organisms.

Nematode parasites of vertebrates (e.g., humans, livestock and companion animals) include gut roundworms, hookworms, pinworms, whipworms, and filarial worms. They can be transmitted in a variety of ways, including by water contamination, skin penetration, biting insects, or by ingestion of contaminated food.

In domesticated animals, nematode control or "de-worming" is essential to the economic viability of livestock producers and is a necessary part of veterinary care of companion animals. Parasitic nematodes cause mortality in animals (e.g., heartworm in dogs and cats) and morbidity as a result of the parasites' inhibiting the ability of the infected animal to absorb nutrients. The parasite-induced nutrient deficiency leads to disease and stunted growth in livestock and companion animals. For instance, in cattle and dairy herds, a single untreated infection with the brown stomach worm can permanently restrict an animal's ability to convert feed into muscle mass or milk.

Two factors contribute to the need for novel anthelmintics and vaccines to control animal parasitic nematodes. First, some of the more prevalent species of parasitic nematodes of livestock are building resistance to the anthelmintic drugs available currently, meaning that these products are losing their efficacy. These developments are not surprising because few effective anthelmintic drugs are available and most have been used continuously. Some parasitic species have developed resistance to most of the anthelmintics (Geents et al. (1997) *Parasitology Today* 13:149-151; Prichard (1994) *Veterinary Parasitology* 54:259-268). The fact that many of the anthelmintic drugs have similar modes of action complicates matters, as the loss of sensitivity of the parasite to one drug is often accompanied by side resistance—that is, resistance to other drugs in the same class (Sangster & Gill (1999) *Parasitology Today* 15(4):141-146). Secondly, there are some issues with toxicity for the major compounds currently available.

Infections by parasitic nematode worms also result in substantial human mortality and morbidity, especially in tropical regions of Africa, Asia, and the Americas. The World Health Organization estimates 2.9 billion people are infected, and in some areas, 85% of the population carries worms. While mortality is rare in proportion to infections, morbidity is substantial and rivals diabetes and lung cancer in worldwide disability adjusted life year (DALY) measurements.

Examples of human parasitic nematodes include hookworms, filarial worms, and pinworms. Hookworms (1.3 billion infections) are the major cause of anemia in millions of children, resulting in growth retardation and impaired cognitive development. Filarial worms invade the lymphatics, resulting in permanently swollen and deformed limbs (elephantiasis), and the eyes, causing African river blindness. The large gut roundworm *Ascaris lumbricoides* infects more than one billion people worldwide and causes malnutrition and obstructive bowel disease. In developed countries, pinworms are common and often transmitted through children in daycare.

Even in asymptomatic parasitic infections, nematodes can still deprive the host of valuable nutrients and increase the ability of other organisms to establish secondary infections. In some cases, infections can cause debilitating illnesses and can result in anemia, diarrhea, dehydration, loss of appetite, or death.

Despite some advances in drug availability and public health infrastructure and the near elimination of one tropical nematode (the water-borne Guinea worm), most nematode diseases have remained intractable problems. Treatment of hookworm diseases with anthelmintic drugs, for instance, has not provided adequate control in regions of high incidence because rapid re-infection occurs after treatment. In fact, over the last 50 years, while nematode infection rates have fallen in the United States, Europe, and Japan, the overall number of infections worldwide has kept pace with the growing world population. Large scale initiatives by regional governments, the World Health Organization, foundations, and pharmaceutical companies are now underway attempting to control nematode infections with currently available tools, including three programs for control of Onchocerciasis (river blindness) in Africa and the Americas using ivermectin and vector control; The Global Alliance to Eliminate Lymphatic Filariasis using DEC, albendazole, and ivermectin; and the highly successful Guinea Worm Eradication Program. Until safe and effective vaccines are discovered to prevent parasitic nematode infections, anthelmintic drugs will continue to be used to control and treat nematode parasitic infections in both humans and domestic animals.

Certain insecticidal oxazoles (U.S. Pat. No. 4,791,124) and thiazoles (U.S. Pat. No. 4,908,357) and nematicidal pyrazoles (U.S. Pat. No. 6,310,049) have been disclosed in the art. The present invention discloses other oxazoles, oxadiazoles and thiadiazoles with surprisingly potent nematicidal activity showing activity comparable to commercial standards. Commercial level nematicidal potency has not previously been demonstrated with oxazoles, oxadiazoles and thiadiazoles. Importantly, these compounds are broadly active against nematodes yet safe to non-target organisms.

U.S. Pat. No. 4,791,124 disclosed certain oxazoles and thiazoles with nematicidal activity against *Meloidogyne incognita* (root knot nematode) at 10 parts per million. However, compounds were not titrated to lower doses and not shown to have potency comparable to commercial standards.

U.S. Pat. No. 6,310,049 disclosed certain nematicidal pyrazoles with activity against root knot nematode. Several pyrazole compounds are shown having activity at 100 ppm in an in vitro assay with a small subset of the compounds having activity at 50 ppm in a soil based greenhouse. One compound is disclosed as having greenhouse activity at 20 ppm and a single compound as having greenhouse activity at 5 ppm. It is not clear if any of these compounds have potency comparable to commercial standards.

Some oxadiazoles compounds having substituted furan or thiophene rings but not unsubstituted furan or thiophene rings are disclosed as being apoptosis inducers and useful as chemotherapeutic against certain cancers (Zhang et al. 2005 J Med Chem. 48(16):5215-23). Notwithstanding some superficial chemical similarities the nematicidal analogs of this invention do not induce apoptosis in mammalian cells and have equal potency against wild type *C. elegans* nematodes and ced-3 or ced-4 *C. elegans* mutants deficient in apoptosis. These analogs are therefore structurally and functionally distinct from the apoptosis inducing oxadiazoles disclosed by Cai et al in U.S. Pat. No. 7,041,685.

SUMMARY

Compositions and processes for controlling nematodes are described herein, e.g., nematodes that infest plants or the situs of plants. Nematodes that parasitize animals can also be controlled using the methods and compounds described herein.

Described herein are nematicidal compositions comprising an effective amount of a compound or a mixture of compounds having any of the formula described herein, for example the compounds shown below.

Described herein is a compound of Formula I or a salt thereof,

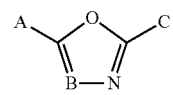

Formula I wherein,

A is an optionally substituted aryl or optionally substituted arylalkyl (e.g., arylC1alkyl or arylC2alkyl) or optionally substituted aryloxo or optionally substituted arylthio, or optionally substituted heteroaryl (including pyridyl, pyrazyl, oxazolyl or isoxazolyl) or optionally substituted heteroarylalkyl (e.g., heteroarylC1alkyl or heteroarylC2alkyl or heteroarylC1alkyl or heteroarylC2alkyl) or optionally substituted heteroaryloxo- or optionally substituted heteroarylthio wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl (C1-C6)alkyl, C6-C10 aryl(C2-C6)alkenyl, C6-C10 aryl(C2-C6)alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

B is C(H) or C(CH$_3$); and

C is an optionally substituted pyrrolyl (including pyrrolyl-1, pyrrolyl-2 or pyrrolyl-3) or optionally substituted pyrroly-loxo (including pyrrolyl-2 or pyrrolyl-3) or optionally substituted pyrrolythio (including pyrrolyl-2 or pyrrolyl-3) or optionally substituted pyrrolylalkyl (e.g., pyrrolyl C1 alkyl or pyrrolyl C2 alkyl) (including pyrrolyl-1, pyrrolyl-2 or pyrrolyl-3) wherein said substituents are selected from the group consisting of methyl, alkyl, cycyl, heterocycl, hydroxyalkyl and halogen.

A compound of Formula Ia or a salt thereof,

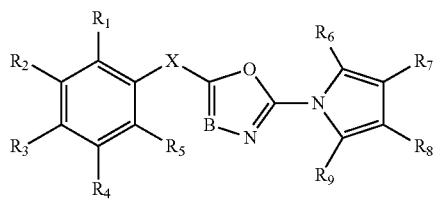

Formula Ia wherein, $R_1$ and $R_5$ are independently selected from hydrogen, CH$_3$, F, Cl, Br, CF$_3$ and OCF$_3$;

$R_2$ and $R_4$ are independently selected from hydrogen, F, Cl, Br, and CF$_3$;

$R_3$ is selected from hydrogen, CH$_3$, CF$_3$, F, Cl, Br, OCF$_3$, OCH$_3$, CN, and CO;

$R_6$, $R_7$, $R_8$ and $R_9$ are independently selected from hydrogen, CH$_3$, alkyl, cykloalkyl, heterocyl, and halogen (Cl, F):

B is C(H) or C(CH$_3$); and

X is a bond, CH$_2$, O or S.

In some cases X is a bond.

In some cases X is CH$_2$, O or S.

In some cases X is CH$_2$.

A compound of Formula II or a salt thereof,

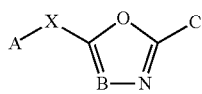

Formula II wherein,

A is an optionally substituted aryl or optionally substituted arylalkyl, or optionally substituted heteroaryl (including pyridyl, pyrazyl, oxazolyl or isoxazolyl) or optionally substituted heteroarylalkyl wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6)alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

B is C(H) or C(CH$_3$);

C is a heteroaryl including thienyl, furanyl, oxazolyl or isoxazolyl each of which can be optionally independently substituted with one or more substituents selected from: fluorine, chlorine, CH$_3$ and OCF$_3$;

and

X is O or S.

A compound of Formula IIa or a salt thereof,

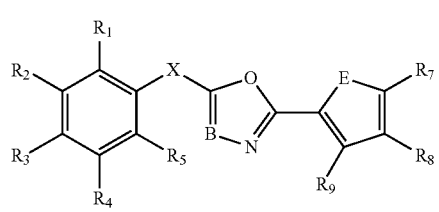

Formula IIa wherein, $R_1$ and $R_5$ are independently selected from hydrogen, CH$_3$, F, Cl, Br, CF$_3$, OCF$_3$ $R_2$ and $R_4$ are independently selected from hydrogen, F, Cl, Br, CF$_3$:

$R_3$ is selected from hydrogen, CH$_3$, CF$_3$, F, Cl, Br, OCF$_3$, OCH$_3$, CN, C(H)O;

$R_7$, $R_8$ and $R_9$ are independently selected from hydrogen, F, Cl, CH$_3$, OCF$_3$;

B is C(H) or C(CH$_3$);

E is O or S;

and

X is O or S.

A compound of Formula IIb or a salt thereof,

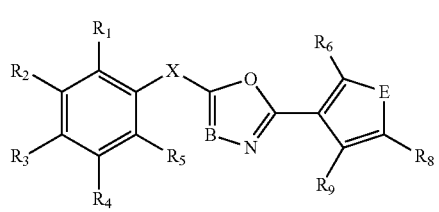

Formula IIb wherein, $R_1$ and $R_5$ are independently selected from hydrogen, CH$_3$, F, Cl, Br, CF$_3$, OCF$_3$;

$R_2$ and $R_4$ are independently selected from hydrogen, F, Cl, Br, CF$_3$;

$R_3$ is selected from hydrogen, CH$_3$, CF$_3$, F, Cl, Br, OCF$_3$, OCH$_3$, CN, CO;

$R_6$, $R_8$ and $R_9$ are independently selected from hydrogen, F, Cl, CH$_3$, OCF$_3$;

B is C(H), C(CH$_3$); and

E is O or S;

X is O or S.

A compound of Formula III or a salt thereof,

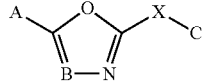

Formula III wherein,

A is an optionally substituted aryl or optionally substituted arylalkyl (e.g., arylC1alkyl or arylC2alkyl), or optionally substituted heteroaryl (including pyridyl, pyrazyl, oxazolyl or isoxazolyl) or optionally substituted heteroarylalkyl (e.g., heteroarylC1alkyl or heteroarylC2alkyl) wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6)alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

B is C(H) or C(CH$_3$);

C is a heteroaryl including thienyl, furanyl, oxazolyl or isoxazolyl each of which can be optionally independently substituted with one or more substituents selected from: fluorine, chlorine, CH$_3$ and OCF$_3$;

and

X is CH$_2$, O or S.

In some cases X is CH$_2$.

In some cases X is O or S.

A compound of Formula IIIa or a salt thereof,

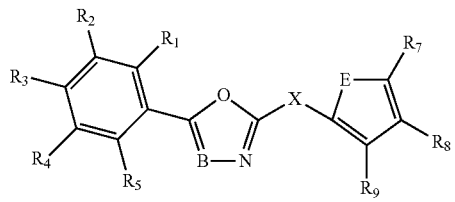

Formula IIIa wherein,

R$_1$ and R$_5$ are independently selected from hydrogen, CH$_3$, F, Cl, Br, CF$_3$, OCF$_3$ R$_2$ and R$_4$ are independently selected from hydrogen, F, Cl, Br, CF$_3$:

R$_3$ is selected from hydrogen, CH$_3$, CF$_3$, F, Cl, Br, OCF$_3$, OCH$_3$, CN, C(H)O;

R$_7$, R$_8$ and R$_9$ are independently selected from hydrogen, F, Cl, CH$_3$, OCF$_3$;

B is C(H) or C(CH$_3$);

E is O or S;

and

X is CH$_2$, O or S.

In some cases X is O or S.

In some cases X is CH$_2$.

A compound of Formula IIIb or a salt thereof,

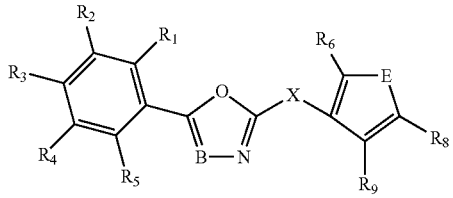

Formula IIIb wherein,

R$_1$ and R$_5$ are independently selected from hydrogen, CH$_3$, F, Cl, Br, CF$_3$, OCF$_3$;

R$_2$ and R$_4$ are independently selected from hydrogen, F, Cl, Br, CF$_3$;

R$_3$ is selected from hydrogen, CH$_3$, CF$_3$, F, Cl, Br, OCF$_3$, OCH$_3$, CN, CO;

R$_6$, R$_8$ and R$_9$ are independently selected from hydrogen, F, Cl, CH$_3$, OCF$_3$;

B is C(H), C(CH$_3$);

E is O or S; and

X is CH$_2$, O or S.

In some cases X is O or S.

In some cases X is CH$_2$.

A compound of Formula IV or a salt thereof,

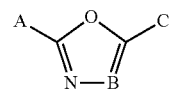

Formula IV wherein,

A is an optionally substituted aryl or optionally substituted arylalkyl (e.g., arylC1alkyl or arylC2alkyl) or optionally substituted aryloxo or optionally substituted arylthio, or optionally substituted heteroaryl (including pyridyl, pyrazyl, oxazolyl or isoxazolyl) or optionally substituted heteroarylalkyl (e.g., heteroarylC1alkyl or heteroarylC2alkyl) or optionally substituted heteroaryloxo- or optionally substituted hetero arylthio wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6)alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

B is C(H) or C(CH$_3$); and

C is an optionally substituted pyrrolyl (including pyrrolyl-1, pyrrolyl-2 or pyrrolyl-3) or optionally substituted pyrroloxo (including pyrrolyl-2 or pyrrolyl-3) or optionally substituted pyrrolythio (including pyrrolyl-2 or pyrrolyl-3) or optionally substituted pyrrolylalkyl (e.g., pyrrolyl C1 alkyl) (including pyrrolyl-1, pyrrolyl-2 or pyrrolyl-3) wherein said substituents are selected from the group consisting of methyl, alkyl, cycyl, heterocycl, hydroxyalkyl and halogen.

A compound of formula IVa or a salt thereof,

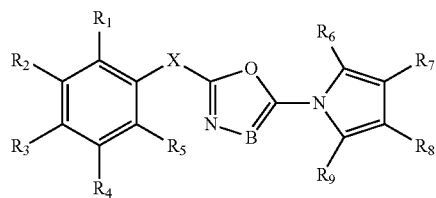

Formula IVa wherein, $R_1$ and $R_5$ are independently selected from hydrogen, $CH_3$, F, Cl, Br, $CF_3$ and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and CO;

$R_6$, $R_7$, $R_8$ and $R_9$ are independently selected from hydrogen, $CH_3$, alkyl, cykloalkyl, heterocyl, and halogen;

B is C(H) or C($CH_3$); and

X is a bond, $CH_2$, O or S.

In some cases X is a bond.

In some cases X is $CH_2$.

In some cases X is O or S.

A compound of Formula V or a salt thereof,

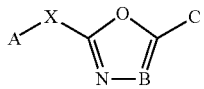

Formula V wherein,

A is an optionally substituted aryl or optionally substituted arylalkyl (e.g., arylC1alkyl or arylC2alkyl), or optionally substituted heteroaryl (including pyridyl, pyrazyl, oxazolyl or isoxazolyl) or optionally substituted heteroarylalkyl (e.g., heteroarylC1alkyl or heteroarylC2alkyl wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6) alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

B is C(H) or C($CH_3$);

C is a heteroaryl including thienyl, furanyl, oxazolyl or isoxazolyl each of which can be optionally independently substituted with one or more substituents selected from: fluorine, chlorine, $CH_3$ and $OCF_3$;

and

X is O or S.

A compound of Formula Va or a salt thereof,

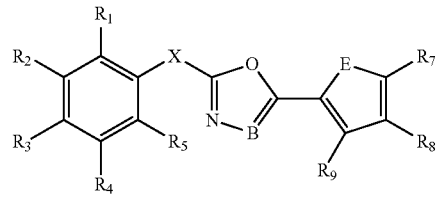

Formula Va wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, C(H)O;

$R_7$, $R_8$ and $R_9$ are independently selected from hydrogen, F, Cl, $CH_3$, $OCF_3$;

B is C(H) or C($CH_3$);

E is O or S;

and

X is O or S.

A compound of Formula Vb or a salt thereof,

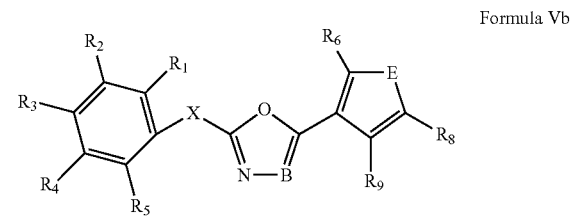

Formula Vb wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, CO;

$R_6$, $R_8$ and $R_9$ are independently selected from hydrogen, F, Cl, $CH_3$, $OCF_3$;

B is C(H), C($CH_3$);

E is O or S; and

X is O or S.

A compound of Formula VI or a salt thereof,

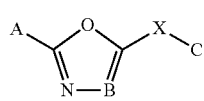

Formula VI wherein,

A is an optionally substituted aryl or optionally substituted arylalkyl (e.g., arylC1alkyl or arylC2alkyl), or optionally substituted heteroaryl (including pyridyl, pyrazyl, oxazolyl or isoxazolyl) or optionally substituted heteroarylalkyl (e.g., heteroryl C1 alkyl) wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6) alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

B is C(H) or C(CH$_3$);

C is a heteroaryl including thienyl, furanyl, oxazolyl or isoxazolyl each of which can be optionally independently substituted with one or more substituents selected from: fluorine, chlorine, CH$_3$ and OCF$_3$;

and

X is CH$_2$, O or S.

In some cases X is O or S.

In some cases X is CH$_2$.

A compound of Formula VIa or a salt thereof,

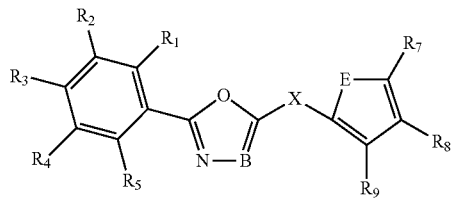

Formula VIa wherein,

R$_1$ and R$_5$ are independently selected from hydrogen, CH$_3$, F, Cl, Br, CF$_3$, OCF$_3$ R$_2$ and R$_4$ are independently selected from hydrogen, F, Cl, Br, CF$_3$:

R$_3$ is selected from hydrogen, CH$_3$, CF$_3$, F, Cl, Br, OCF$_3$, OCH$_3$, CN, C(H)O;

R$_7$, R$_8$ and R$_9$ are independently selected from hydrogen, F, Cl, CH$_3$, OCF$_3$;

B is C(H) or C(CH$_3$);

E is O or S;

X is O or S.

A compound of Formula VIb or a salt thereof,

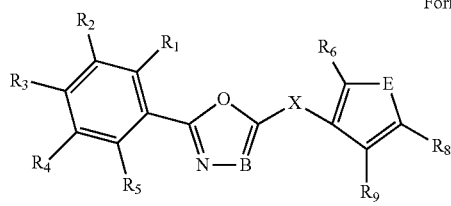

Formula VIb wherein,

R$_1$ and R$_5$ are independently selected from hydrogen, CH$_3$, F, Cl, Br, CF$_3$, OCF$_3$;

R$_2$ and R$_4$ are independently selected from hydrogen, F, Cl, Br, CF$_3$;

R$_3$ is selected from hydrogen, CH$_3$, CF$_3$, F, Cl, Br, OCF$_3$, OCH$_3$, CN, CO;

R$_6$, R$_8$ and R$_9$ are independently selected from hydrogen, F, Cl, CH$_3$, OCF$_3$;

B is C(H), C(CH$_3$);

E is O or S;

and

X is CH$_2$, O or S.

In some cases X is CH$_2$.

In some cases X is O or S.

A compound of Formula VII or a salt thereof

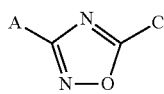

Formula VII wherein,

A is an optionally substituted aryl or optionally substituted arylalkyl (e.g., arylC1alkyl or arylC2alkyl) or optionally substituted aryloxo or optionally substituted arylthio, or optionally substituted heteroaryl (including pyridyl, pyrazyl, oxazolyl or isoxazolyl) or optionally substituted heteroarylalkyl (e.g., heteroarylC1alkyl or heteroarylC2alkyl) or optionally substituted heteroaryloxo- or optionally substituted hetero arylthio wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6) alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

and

C is an optionally substituted pyrrolyl (including pyrrolyl-1, pyrrolyl-2 or pyrrolyl-3) or optionally substituted pyrroly-loxo (including pyrrolyl-2 or pyrrolyl-3) or optionally substituted pyrrolythio (including pyrrolyl-2 or pyrrolyl-3) or optionally substituted pyrrolylalkyl (e.g., pyrrolyl C1 alkyl) (including pyrrolyl-1, pyrrolyl-2 or pyrrolyl-3) wherein said substituents are selected from the group consisting of methyl, alkyl, cycyl, heterocycl, hydroxyalkyl and halogen.

A compound of formula VIIa or a salt thereof,

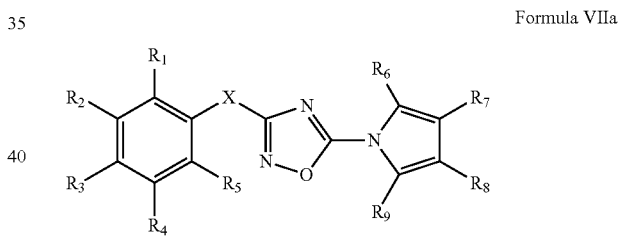

Formula VIIa wherein,

R$_1$ and R$_5$ are independently selected from hydrogen, CH$_3$, F, Cl, Br, CF$_3$ and OCF$_3$;

R$_2$ and R$_4$ are independently selected from hydrogen, F, Cl, Br, and CF$_3$;

R$_3$ is selected from hydrogen, CH$_3$, CF$_3$, F, Cl, Br, OCF$_3$, OCH$_3$, CN, and CO;

R$_6$, R$_7$, R$_8$ and R$_9$ are independently selected from hydrogen, CH3, alkyl, cykloalkyl, heterocyl, and halogen;

and

X is a bond, CH$_2$, O or S.

In some cases X is a bond.

In some cases X is O or S.

In some cases X is CH$_2$.

A compound of Formula VIII or a salt thereof,

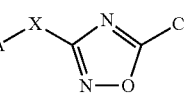

Formula VIII wherein,

A is an optionally substituted aryl or optionally substituted arylalkyl, or optionally substituted heteroaryl (including pyridyl, pyrazyl, oxazolyl or isoxazolyl) or optionally substituted heteroarylalkyl wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6)alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

B is C(H) or C(CH$_3$);

C is a heteroaryl including thienyl, furanyl, oxazolyl or isoxazolyl each of which can be optionally independently substituted with one or more substituents selected from: fluorine, chlorine, CH$_3$ and OCF$_3$;

and

X is O or S.

A compound of Formula VIIIa or salt thereof,

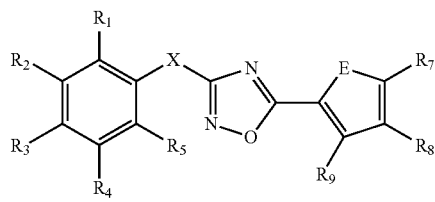

Formula VIIIa wherein, $R_1$ and $R_5$ are independently selected from hydrogen, CH$_3$, F, Cl, Br, CF$_3$, OCF$_3$ $R_2$ and $R_4$ are independently selected from hydrogen, F, Cl, Br, CF$_3$:

$R_3$ is selected from hydrogen, CH$_3$, CF$_3$, F, Cl, Br, OCF$_3$, OCH$_3$, CN, C(H)O;

$R_7$, $R_8$ and $R_9$ are independently selected from hydrogen, F, Cl, CH$_3$, OCF$_3$;

E is O or S;

and

X is O or S.

A compound of Formula VIIIb or a salt thereof,

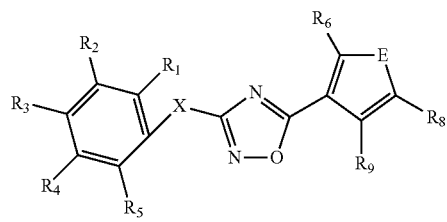

Formula VIIIb wherein, $R_1$ and $R_5$ are independently selected from hydrogen, CH$_3$, F, Cl, Br, CF$_3$, OCF$_3$;

$R_2$ and $R_4$ are independently selected from hydrogen, F, Cl, Br, CF$_3$;

$R_3$ is selected from hydrogen, CH$_3$, CF$_3$, F, Cl, Br, OCF$_3$, OCH$_3$, CN, CO;

$R_6$, $R_8$ and $R_9$ are independently selected from hydrogen, F, Cl, CH$_3$, OCF$_3$;

E is O or S; and

X is O or S,

A compound of Formula IX or a salt thereof,

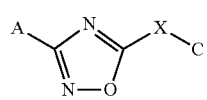

Formula IX

A is an optionally substituted aryl or optionally substituted arylalkyl (e.g., arylC1alkyl or arylC2alkyl), or optionally substituted heteroaryl (including pyridyl, pyrazyl, oxazolyl or isoxazolyl) or optionally substituted heteroarylalkyl (e.g., heteroarylC1alkyl or heteroarylC2alkyl) wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6)alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

B is C(H) or C(CH$_3$);

C is a heteroaryl including thienyl, furanyl, oxazolyl or isoxazolyl each of which can be optionally independently substituted with one or more substituents selected from: fluorine, chlorine, CH$_3$ and OCF$_3$;

and

X is CH$_2$, O or S.

In some cases X is O or S.

In some cases X is CH$_2$.

A compound of Formula IXa or a salt thereof,

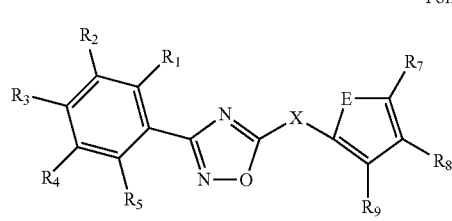

Formula IXa wherein, $R_1$ and $R_5$ are independently selected from hydrogen, CH$_3$, F, Cl, Br, CF$_3$, OCF$_3$;

$R_2$ and $R_4$ are independently selected from hydrogen, F, Cl, Br, CF$_3$;

$R_3$ is selected from hydrogen, CH$_3$, CF$_3$, F, Cl, Br, OCF$_3$, OCH$_3$, CN, C(H)O;

$R_7$, $R_8$ and $R_9$ are independently selected from hydrogen, F, Cl, CH$_3$, OCF$_3$;

E is O or S;

and

X is CH$_2$, O or S.

In some cases X is O or S.

In some cases X is CH$_2$.

A compound of Formula IXb or a salt thereof

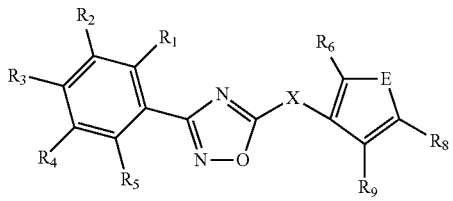

Formula IXb wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, CO;

$R_6$, $R_8$ and $R_9$ are independently selected from hydrogen, F, Cl, $CH_3$, $OCF_3$;

E is O or S; and

X is $CH_2$, O or S.

In some cases X is O or S.

In some cases X is $CH_2$.

A compound of Formula X or a salt thereof,

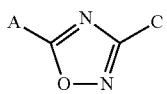

Formula X

A is an optionally substituted aryl or optionally substituted arylalkyl (e.g., arylC1alkyl or arylC2alkyl) or optionally substituted aryloxo or optionally substituted arylthio, or optionally substituted heteroaryl (including pyridyl, pyrazyl, oxazolyl or isoxazolyl) or optionally substituted heteroarylalkyl (e.g., heteroarylC1alkyl or heteroarylC2alkyl) or optionally substituted heteroaryloxo- or optionally substituted hetero arylthio wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6) alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

and

C is an optionally substituted pyrrolyl (including pyrrolyl-1, pyrrolyl-2 or pyrrolyl-3) or optionally substituted pyrroloxo (including pyrrolyl-2 or pyrrolyl-3) or optionally substituted pyrrolythio (including pyrrolyl-2 or pyrrolyl-3) or optionally substituted pyrrolylalkyl (e.g., pyrrol C1 alkyl) (including pyrrolyl-1, pyrrolyl-2 or pyrrolyl-3) wherein said substituents are selected from the group consisting of methyl, alkyl, cycyl, heterocycl, hydroxyalkyl and halogen, A compound of formula Xa or a salt thereof,

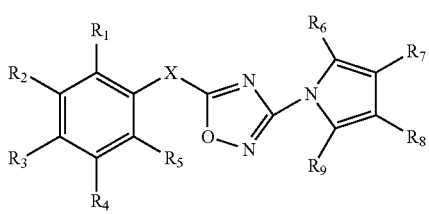

Formula Xa wherein, $R_1$ and $R_5$ are independently selected from hydrogen, $CH_3$, F, Cl, Br, $CF_3$ and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and CO;

$R_6$, $R_7$, $R_8$ and $R_9$ are independently selected from hydrogen, CH3, alkyl, cykloalkyl, heterocyl, and halogen;

and

X is a bond, $CH_2$, O or S.

In some cases X is O or S.

In some cases X is $CH_2$.

A compound of Formula XI or a salt thereof,

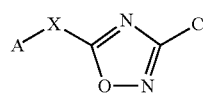

Formula XI wherein,

A is an optionally substituted aryl or optionally substituted arylalkyl, or optionally substituted heteroaryl (including pyridyl, pyrazyl, oxazolyl or isoxazolyl) or optionally substituted heteroarylalkyl wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6)alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

C is heterocycl including thienyl, furanyl, oxazolyl or isoxazolyl each of which can be optionally independently substituted with one or more substituents selected from: fluorine, chlorine, $CH_3$ and $OCF_3$;

and

X is O or S

A compound of formula XIa or a salt thereof,

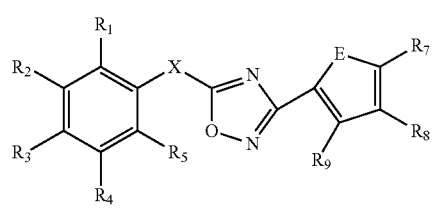

Formula XIa wherein,
R₁ and R₅ are independently selected from hydrogen, CH₃, F, Cl, Br, CF₃, OCF₃
R₂ and R₄ are independently selected from hydrogen, F, Cl, Br, CF₃:
R₃ is selected from hydrogen, CH₃, CF₃, F, Cl, Br, OCF₃, OCH₃, CN, C(H)O;
R₇, R₈ and R₉ are independently selected from hydrogen, F, Cl, CH₃, OCF₃;
E is O or S
and
X is O or S
A compound having the Formula XIb or a salt thereof,

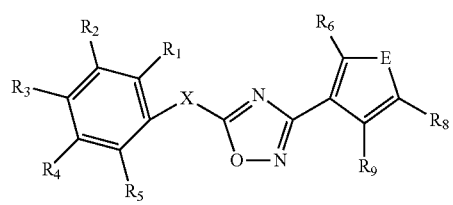

Formula XIb wherein,
R₁ and R₅ are independently selected from hydrogen, CH₃, F, Cl, Br, CF₃, OCF₃;
R₂ and R₄ are independently selected from hydrogen, F, Cl, Br, CF₃;
R₃ is selected from hydrogen, CH₃, CF₃, F, Cl, Br, OCF₃, OCH₃, CN, CO;
R₆, R₈ and R₉ are independently selected from hydrogen, F, Cl, CH₃, OCF₃;
E is O or S; and
X is O or S.
A compound of Formula XII or a salt thereof,

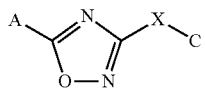

Formula XII wherein,
A is an optionally substituted aryl or optionally substituted arylalkyl (e.g., arylC1alkyl or arylC2alkyl), or optionally substituted heteroaryl (including pyridyl, pyrazyl, oxazolyl or isoxazolyl) or optionally substituted heteroarylalkyl (e.g., heteroarylC1alkyl or heteroarylC2alkyl) wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6) alkyl, C6-C10 aryl(C2-C6)alkenyl, C6-C10 aryl(C2-C6) alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;
C is a heteroaryl including thienyl, furanyl, oxazolyl or isoxazolyl each of which can be optionally independently substituted with one or more substituents selected from: fluorine, chlorine, CH₃ and OCF₃;
and
X is CH₂, O or S.
In some cases X is O or S.
In some cases X is CH₂.
A compound of the Formula XIIa or salt thereof,

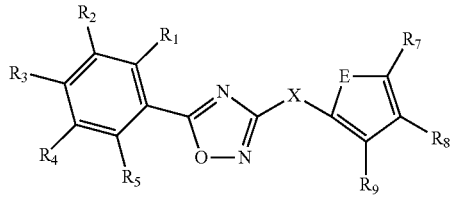

Formula XIIa wherein,
R₁ and R₅ are independently selected from hydrogen, CH₃, F, Cl, Br, CF₃, OCF₃;
R₂ and R₄ are independently selected from hydrogen, F, Cl, Br, CF₃:
R₃ is selected from hydrogen, CH₃, CF₃, F, Cl, Br, OCF₃, OCH₃, CN, C(H)O;
R₇, R₈ and R₉ are independently selected from hydrogen, F, Cl, CH₃, OCF₃;
B is C(H) or C(CH₃);
E is O or S;
and
X is CH₂, O or S.
In some cases X is O or S.
In some cases X is CH₂.
A compound of Formula XIIb or a salt thereof,

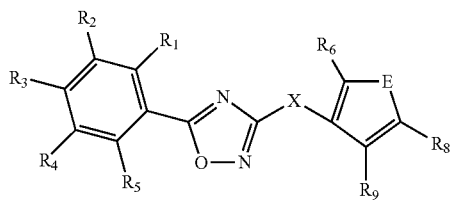

Formula XIIb wherein,
R₁ and R₅ are independently selected from hydrogen, CH₃, F, Cl, Br, CF₃, OCF₃;
R₂ and R₄ are independently selected from hydrogen, F, Cl, Br, CF₃;
R₃ is selected from hydrogen, CH₃, CF₃, F, Cl, Br, OCF₃, OCH₃, CN, CO;
R₆, R₈ and R₉ are independently selected from hydrogen, F, Cl, CH₃, OCF₃;
E is O or S; and
X is CH₂, O or S.
In some cases X is O or S.
In some cases X is CH₂.
A compound of Formula XIII or a salt thereof,

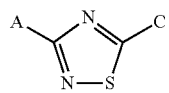

Formula XIII

A is an optionally substituted aryl or optionally substituted arylalkyl (e.g., arylC1alkyl or arylC2alkyl) or optionally substituted aryloxo or optionally substituted arylthio, or optionally substituted heteroaryl (including pyridyl, pyrazyl, oxazolyl or isoxazolyl) or optionally substituted heteroarylalkyl or optionally substituted heteroaryloxo- or optionally substituted hetero arylthio wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6) alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

and

C is an optionally substituted pyrrolyl (including pyrrolyl-1, pyrrolyl-2 or pyrrolyl-3) or optionally substituted pyrroly-loxo (including pyrrolyl-2 or pyrrolyl-3) or optionally substituted pyrrolythio (including pyrrolyl-2 or pyrrolyl-3) or optionally substituted pyrrolylalkyl (including pyrrolyl-1, pyrrolyl-2 or pyrrolyl-3) wherein said substituents are selected from the group consisting of methyl, alkyl, cycyl, heterocycl, hydroxyalkyl and halogen.

A compound of formula XIIIa or a salt thereof,

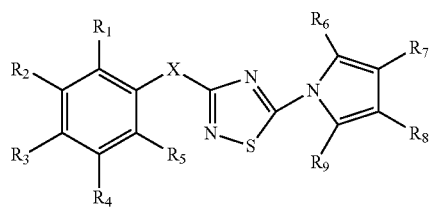

Formula XIIIa wherein, $R_1$ and $R_5$ are independently selected from hydrogen, $CH_3$, F, Cl, Br, $CF_3$ and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and CO;

$R_6$, $R_7$, $R_8$ and $R_9$ are independently selected from hydrogen, CH3, alkyl, cykloalkyl, heterocyl, and halogen; and X is a bond, $CH_2$, O or S.

In some cases X is a bond.

In some cases X is O or S.

In some cases X is $CH_2$.

A compound of Formula XIV or a salt thereof,

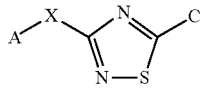

Formula XIV wherein,

A is an optionally substituted aryl or optionally substituted arylalkyl (e.g., arylC1alkyl or arylC2alkyl), or optionally substituted heteroaryl (including pyridyl, pyrazyl, oxazolyl or isoxazolyl) or optionally substituted heteroarylalkyl (e.g., heteroarylC1alkyl or heteroarylC2alkyl) wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6) alkyl, C6-C10 aryl(C2-C6)alkenyl, C6-C10 aryl(C2-C6) alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

C is heteroaryl including thienyl, furanyl, oxazolyl or isoxazolyl each of which can be optionally independently substituted with one or more substituents selected from: fluorine, chlorine, $CH_3$ and $OCF_3$;

and

X is O or S.

A compound of Formula XIVa or a salt thereof,

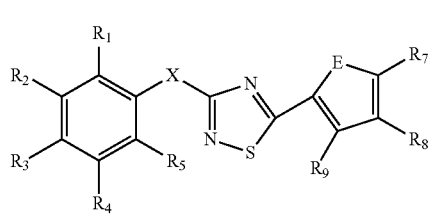

Formula XIVa wherein, $R_1$ and $R_5$ are independently selected from hydrogen, $CH_3$, F, Cl, Br, $CF_3$, $OCF_3$ $R_2$ and $R_4$ are independently selected from hydrogen, F, Cl, Br, $CF_3$:

$R_3$ is selected from hydrogen, $CH_3$, $CF_3$, F, Cl, Br, $OCF_3$, $OCH_3$, CN, C(H)O;

$R_7$, $R_8$ and $R_9$ are independently selected from hydrogen, F, Cl, $CH_3$, $OCF_3$;

E is O or S;

and

X is O or S.

A compound of Formula XIVb or a salt thereof,

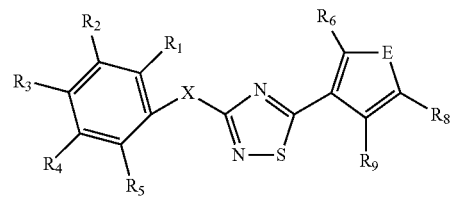

Formula XIVb wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, CO;

$R_6$, $R_7$ and $R_9$ are independently selected from hydrogen, F, Cl, $CH_3$, $OCF_3$;

E is O or S; and

X is O or S.

A compound of Formula XV or a salt thereof,

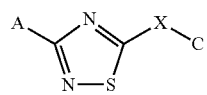

Formula XV wherein,

A is an optionally substituted aryl or optionally substituted arylalkyl (e.g., arylC1alkyl or arylC2alkyl), or optionally substituted heteroaryl (including pyridyl, pyrazyl, oxazolyl or isoxazolyl) or optionally substituted heteroarylalkyl (e.g., heteroarylC1alkyl or heteroarylC2alkyl) wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6) alkyl, C6-C10 aryl(C2-C6)alkenyl, C6-C10 aryl(C2-C6) alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

C is a heteroaryl including thienyl, furanyl, oxazolyl or isoxazolyl each of which can be optionally independently substituted with one or more substituents selected from: fluorine, chlorine, $CH_3$ and $OCF_3$;

and

X is $CH_2$, O or S.

In some cases X is O or S.

In some cases X is $CH_2$.

A compound of Formula XVa or a salt thereof,

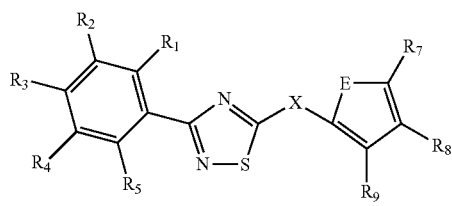

Formula Xva wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$:

$R_3$ is selected from hydrogen, $CH_3$, $CF_3$, F, Cl, Br, $OCF_3$, $OCH_3$, CN, C(H)O;

$R_7$, $R_8$ and $R_9$ are independently selected from hydrogen, F, Cl, $CH_3$, $OCF_3$;

E is O or S;

and

X is $CH_2$, O or S.

In some cases X is O or S.

In some cases X is $CH_2$.

A compound of Formula XVb or a salt thereof,

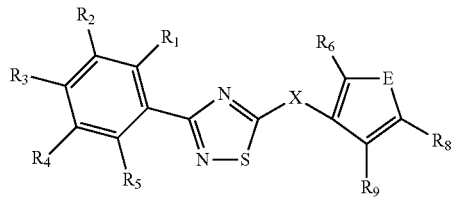

Formula XVb wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, CO;

$R_6$, $R_8$ and $R_9$ are independently selected from hydrogen, F, Cl, $CH_3$, $OCF_3$;

E is O or S; and

X is $CH_2$, O or S.

A compound of Formula XVI or a salt thereof,

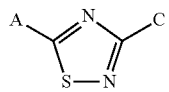

Formula XVI wherein,

A is an optionally substituted aryl or optionally substituted arylalkyl (e.g., arylC1alkyl or arylC2alkyl) or optionally substituted aryloxo or optionally substituted arylthio, or optionally substituted heteroaryl (including pyridyl, pyrazyl, oxazolyl or isoxazolyl) or optionally substituted heteroarylalkyl (e.g., heteroarylC1alkyl or heteroarylC2alkyl) or optionally substituted heteroaryloxo- or optionally substituted hetero arylthio wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6) alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

and

C is an optionally substituted pyrrolyl (including pyrrolyl-1, pyrrolyl-2 or pyrrolyl-3) or optionally substituted pyrrolyloxo (including pyrrolyl-2 or pyrrolyl-3) or optionally substituted pyrrolythio (including pyrrolyl-2 or pyrrolyl-3) or optionally substituted pyrrolylalkyl (including pyrrolyl-1, pyrrolyl-2 or pyrrolyl-3) wherein said substituents are selected from the group consisting of methyl, alkyl, cycyl, heterocycl, hydroxyalkyl and halogen.

A compound of formula XVIa or a salt thereof,

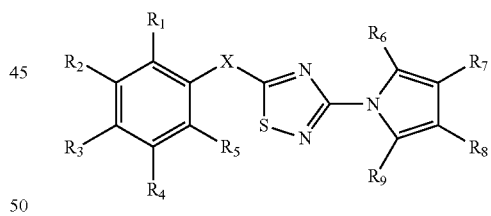

Formula XVIa wherein, $R_1$ and $R_5$ are independently selected from hydrogen, $CH_3$, F, Cl, Br, $CF_3$ and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and CO;

$R_6$, $R_7$, $R_8$ and $R_9$ are independently selected from hydrogen, $CH_3$, alkyl, cykloalkyl, heterocyl, and halogen;

and

X is a bond, $CH_2$, O or S.

In some cases X is a bond.

In some cases X is O or S.

In some cases X is $CH_2$.

A compound of Formula XVII or a salt thereof,

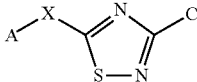

Formula XVII wherein,

A is an optionally substituted aryl or optionally substituted arylalkyl (e.g., arylC1alkyl or arylC2alkyl), or optionally substituted heteroaryl (including pyridyl, pyrazyl, oxazolyl or isoxazolyl) or optionally substituted heteroarylalkyl (e.g., heteroarylC1alkyl or heteroarylC2alkyl) wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6) alkyl, C6-C10 aryl(C2-C6)alkenyl, C6-C10 aryl(C2-C6) alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

C is a heteroaryl including thienyl, furanyl, oxazolyl or isoxazolyl each of which can be optionally independently substituted with one or more substituents selected from: fluorine, chlorine, $CH_3$ and $OCF_3$; and X is O or S.

A compound of formula XVIIa or a salt thereof,

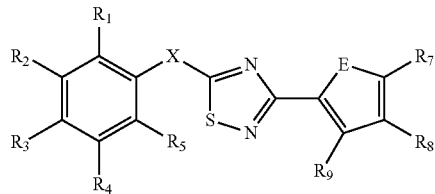

Formula XVIIa wherein, $R_1$ and $R_5$ are independently selected from hydrogen, $CH_3$, F, Cl, Br, $CF_3$, $OCF_3$ $R_2$ and $R_4$ are independently selected from hydrogen, F, Cl, Br, $CF_3$:

$R_3$ is selected from hydrogen, $CH_3$, $CF_3$, F, Cl, Br, $OCF_3$, $OCH_3$, CN, C(H)O;

$R_7$, $R_8$ and $R_9$ are independently selected from hydrogen, F, Cl, $CH_3$, $OCF_3$;

E is O or S; and

X is O or S;

A compound of formula XVIIb or a salt thereof,

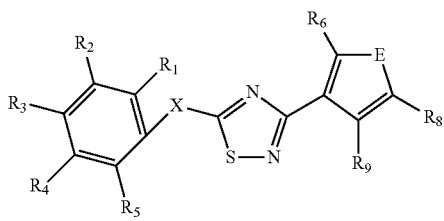

Formula XVIIb wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, CO;

$R_6$, $R_8$ and $R_9$ are independently selected from hydrogen, F, Cl, $CH_3$, $OCF_3$;

E is O or S; and

X is O or S.

A compound of Formula XVIII or a salt thereof,

Formula XVIII wherein,

A is an optionally substituted aryl or optionally substituted arylalkyl (e.g., arylC1alkyl or arylC2alkyl), or optionally substituted heteroaryl (including pyridyl, pyrazyl, oxazolyl or isoxazolyl) or optionally substituted heteroarylalkyl (e.g., heteroarylC1alkyl or heteroarylC2alkyl) wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6) alkyl, C6-C10 aryl(C2-C6)alkenyl, C6-C10 aryl(C2-C6) alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

C is heteroaryl including thienyl, furanyl, oxazolyl or isoxazolyl each of which can be optionally independently substituted with one or more substituents selected from: fluorine, chlorine, $CH_3$ and $OCF_3$; and X is $CH_2$, O or S.

In some cases X is O or S.

In some cases X is $CH_2$.

A compound of formula XVIIIa or a salt thereof,

Formula XVIIIa wherein, $R_1$ and $R_5$ are independently selected from hydrogen, $CH_3$, F, Cl, Br, $CF_3$, OCF;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, C(H)O;

$R_7$, $R_8$ and $R_9$ are independently selected from hydrogen, F, Cl, $CH_3$, $OCF_3$;

E is O or S;

and

X is $CH_2$, O or S.

In some cases X is O or S.

In some cases X is $CH_2$.

A compound of formula XVIIIb or a salt thereof,

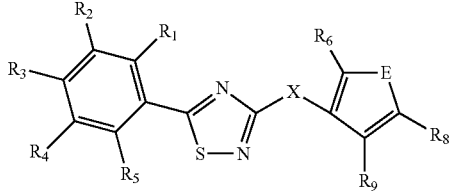

Formula XVIIIb wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, CO;

$R_6$, $R_8$ and $R_9$ are independently selected from hydrogen, F, Cl, $CH_3$, $OCF_3$;

E is O or S; and

X is $CH_2$, O or S.

In some cases X is O or S.

In some cases X is $CH_2$.

A compound of Formula XIX or a salt thereof,

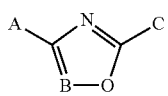

Formula XIX wherein,

A is an optionally substituted aryl or optionally substituted arylalkyl (e.g., arylC1alkyl or arylC2alkyl) or optionally substituted aryloxo or optionally substituted arylthio, or optionally substituted heteroaryl (including pyridyl, pyrazyl, oxazolyl or isoxazolyl) or optionally substituted heteroarylalkyl or optionally substituted heteroaryloxo- or optionally substituted hetero arylthio wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6) alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

B is C(H) or $C(CH_3)$; and

C is an optionally substituted heteroaryl, including thienyl, furanyl, oxazolyl, isoxazolyl and pyrrolyl(-1,-2 or-3), or optionally substituted heteroarylalkyl (e.g., heteroarylC1alkyl or heteroarylC2alkyl), including pyrroylalkyl (e.g, pyrrol C1 alkyl), furanylalkyl, thienylalkyl, oxazolylalkyl or isoxazolyl alkyl, or optionally substituted hetroaryloxo including pyrroyloxo, furanyloxo or thienyloxo, optionally substituted heteroarylthio including pyrrolylthio, furanylthio and thienylthio wherein said substituents are selected from the group consisting of methyl, alkyl, cycyl, heterocycl, hydroxyalkyl, halogen (F or CL), and $OCF_3$.

A compound of formula XIXa or a salt thereof,

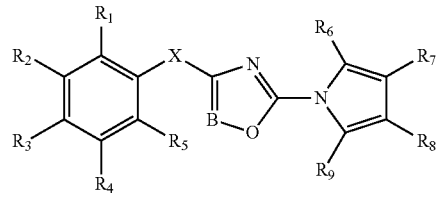

Formula XIXa wherein, $R_1$ and $R_5$ are independently selected from hydrogen, $CH_3$, F, Cl, Br, $CF_3$ and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and CO;

$R_6$, $R_7$, $R_8$ and $R_9$ are independently selected from hydrogen, $CH_3$, alkyl, cykloalkyl, heterocyl, and halogen;

B is C(H) or $C(CH_3)$; and

X is a bond, $CH_2$, O or S.

In some cases X is a bond.

In some cases X is O or S.

In some cases X is $CH_2$.

A compound of formula XIXb or a salt thereof,

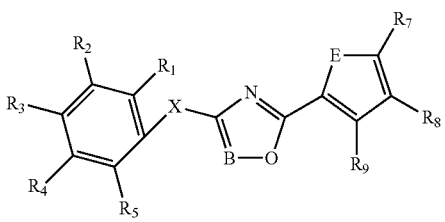

Formula XIXb wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, C(H)O;

$R_7$, $R_8$ and $R_9$ are independently selected from hydrogen, F, Cl, $CH_3$, $OCF_3$;

E is O or S;

B is C(H) or $C(CH_3)$; and

X is a bond, $CH_2$, O or S.

A compound of formula XIXc or a salt thereof,

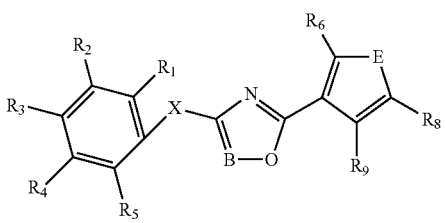

Formula XIXc wherein,

R₁ and R₅ are independently selected from hydrogen, CH₃, F, Cl, Br, CF₃, OCF₃;

R₂ and R₄ are independently selected from hydrogen, F, Cl, Br, CF₃;

R₃ is selected from hydrogen, CH₃, CF₃, F, Cl, Br, OCF₃, OCH₃, CN, CO;

R₆, R₈ and R₉ are independently selected from hydrogen, F, Cl, CH₃, OCF₃;

B is C(H) or C(CH₃);

E is O or S; and

X is a bond, CH₂, O or S.

A compound of formula XIXd or a salt thereof,

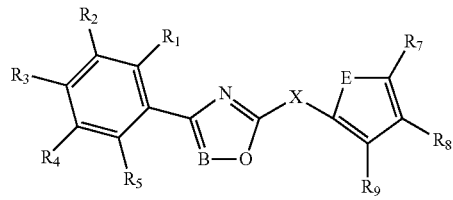

Formula XIXd wherein,

R₁ and R₅ are independently selected from hydrogen, CH₃, F, Cl, Br, CF₃, OCF₃;

R₂ and R₄ are independently selected from hydrogen, F, Cl, Br, CF₃;

R₃ is selected from hydrogen, CH₃, CF₃, F, Cl, Br, OCF₃, OCH₃, CN, C(H)O;

R₇, R₈ and R₉ are independently selected from hydrogen, F, Cl, CH₃, OCF₃;

E is O or S;

B is C(H) or C(CH₃); and

X is a bond, CH₂, O or S.

In some cases X is a bond.

In some cases X is O or S.

In some cases X is CH₂.

A compound of formula XIXe or a salt thereof,

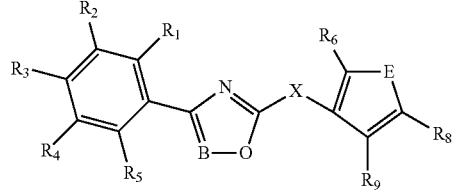

Formula XIXe wherein,

R₁ and R₅ are independently selected from hydrogen, CH₃, F, Cl, Br, CF₃, OCF₃;

R₂ and R₄ are independently selected from hydrogen, F, Cl, Br, CF₃;

R₃ is selected from hydrogen, CH₃, CF₃, F, Cl, Br, OCF₃, OCH₃, CN, CO;

R₆, R₈ and R₉ are independently selected from hydrogen, F, Cl, CH₃, OCF₃;

B is C(H) or C(CH₃); and

E is O or S;

X is a bond, CH₂, O or S.

A compound of Formula XX or a salt thereof,

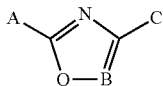

Formula XX wherein,

A is an optionally substituted aryl or optionally substituted arylalkyl (e.g., arylC1alkyl or arylC2alkyl) or optionally substituted aryloxo or optionally substituted arylthio, or optionally substituted heteroaryl (including pyridyl, pyrazyl, oxazolyl or isoxazolyl) or optionally substituted heteroarylalkyl (e.g., heteroarylC1alkyl or heteroarylC2alkyl) or optionally substituted heteroaryloxo- or optionally substituted hetero arylthio wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6) alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

B is C(H) or C(CH₃); and

C is an optionally substituted heteroaryl, including thienyl, furanyl, oxazolyl, isoxazolyl and pyrrolyl (-1,-2 or-3), or optionally substituted heteroarylalkyl (e.g., heteroarylC1alkyl or heteroarylC2alkyl), including pyrroylalkyl (e.g., pyrrol C1 alkyl), furanylalkyl, thienylalkyl, oxazolylalkyl or isoxazolyl alkyl, or optionally substituted hetroaryloxo including pyrroyloxo, furanyloxo or thienyloxo, optionally substituted heteroarylthio including pyrrolylthio, furanylthio and thienylthio wherein said substituents are selected from the group consisting of methyl, alkyl, cycyl, heterocycl, hydroxyalkyl, halogen (F or Cl), and OCF₃.

A compound of Formula XXa or a salt thereof,

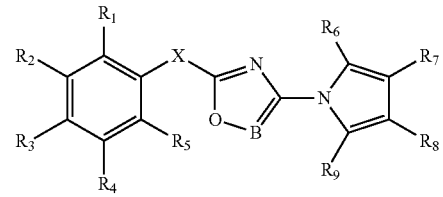

Formula XXa wherein,

R₁ and R₅ are independently selected from hydrogen, CH₃, F, Cl, Br, CF₃ and OCF₃;

R₂ and R₄ are independently selected from hydrogen, F, Cl, Br, and CF₃;

R₃ is selected from hydrogen, CH₃, CF₃, F, Cl, Br, OCF₃, OCH₃, CN, and CO;

R₆, R₇, R₈ and R₉ are independently selected from hydrogen, CH3, alkyl, cykloalkyl, heterocyl, and halogen;

B is C(H) or C(CH₃); and

X is a bond, CH₂, O or S.

In some cases X is a bond.

In some cases X is O or S.

In some cases X is CH₂.

A compound of Formula XXb or a salt thereof,

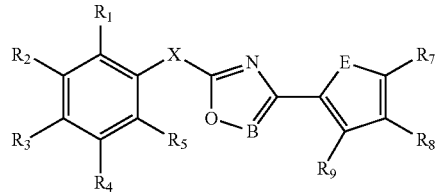

Formula XXb wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, C(H)O;

$R_7$, $R_8$ and $R_9$ are independently selected from hydrogen, F, Cl, $CH_3$, $OCF_3$;

E is O or S;

B is C(H) or C($CH_3$); and

X is a bond, $CH_2$, O or S.

In some cases X is a bond.

In some cases X is O or S.

In some cases X is $CH_2$.

A compound of having Formula XXc or a salt thereof,

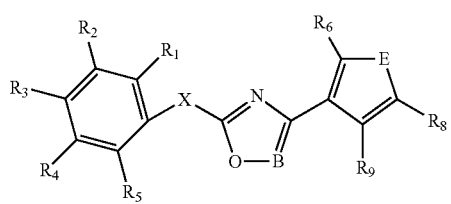

Formula XXc wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, CO;

$R_6$, $R_8$ and $R_9$ are independently selected from hydrogen, F, Cl, $CH_3$, $OCF_3$;

B is C(H) or C($CH_3$);

E is O or S; and

X is a bond, $CH_2$, O or S.

In some cases X is a bond.

In some cases X is O or S.

In some cases X is $CH_2$.

A compound of Formula XXd or a salt thereof,

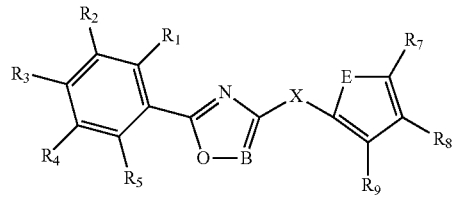

Formula XXd wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, C(H)O;

$R_7$, $R_8$ and $R_9$ are independently selected from hydrogen, F, Cl, $CH_3$, $OCF_3$;

E is O or S;

B is C(H) or C($CH_3$); and

X is a atom, $CH_2$, O or S.

A compound of Formula XXe or a salt thereof,

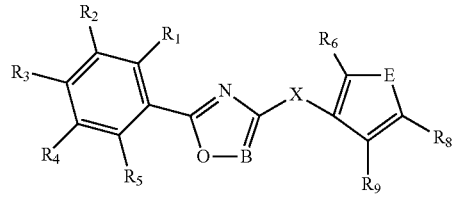

Formula XXe wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, CO;

$R_6$, $R_8$ and $R_9$ are independently selected from hydrogen, F, Cl, $CH_3$, $OCF_3$;

B is C(H) or C($CH_3$);

E is O or S; and

X is a bond, $CH_2$, O or S.

In certain embodiments: the compound has Formula Ia and X is a bond; the compound has Formula VIIIb and X and E are both O; the compound has Formula XIXb and X is a bond and E is O.

Also described herein is a method for control of unwanted nematodes, the method comprising administering to mammals, birds, or their food, plants, seeds or soil a composition comprising an effective amount of a compound of any of Formulas I, Ia, II, IIa, IIb, III, IIIa, IIIb, IV, IVa, V, Va, Vb, VI, VIa, VIb, VII, VIIa, VIII, VIIIa, VIIIb, IX, IXa, IXb, X, Xa, XI, XIa, XIb, XII, XIIa, XIIb, XIII, XIIIa, XIV, XIVa, XIVb, XV, XVa, XVb, XVI, XVIa, XVII, XVIIa, XVIIb, XVIII, XVIIIa, XVIIIb, XIX, XIXa, XIXb, XIXc, XIXd, XIXe, XX, XXa, XXb, XXc, XXd and XXe.

In some cases the method entails controlling plant parasitic nematodes and comprises administering to plant subject to attack by such nematodes, the seeds of such plants or the soil in which such plants are grown or are to be planted.

Also described is a nematicidal composition comprising a compound of any of Formulas I, Ia, II, IIa, IIb, III, IIIa, IIIb, IV, IVa, V, Va, Vb, VI, VIa, VIb, VII, VIIa, VIII, VIIIa, VIIIb, IX, IXa, IXb, X, Xa, XI, XIa, XIb, XII, XIIa, XIIb, XIII, XIIIa, XIV, XIVa, XIVb, XV, XVa, XVb, XVI, XVIa, XVII, XVIIa, XVIIb, XVIII, XVIIIa, XVIIIb, XIX, XIXa, XIXb, XIXc, XIXd, XIXe, XX, XXa, XXb, XXc, XXd and XXe at a concentration sufficient to reduce the viability of a parasitic nematode.

In some cases, the nematicidal composition further includes an aqueous surfactant. Examples of surfactants that can be used include, Span 20, Span 40, Span 80, Span 85, Tween 20, Tween 40, Tween 80, Tween 85, Triton X 100, Makon 10, Igepal CO 630, Brij 35, Brij 97, Tergitol TMN 6, Dowfax 3B2, Physan and Toximul TA 15. In some cases, the nematicidal composition further includes a permeation enhancer (e.g., cyclodextrin). In some cases, the nematicidal composition further includes a co-solvent. Examples of co-solvents that can be used include ethyl lactate, methyl soyate/ethyl lactate co-solvent blends (e.g., Steposol), isopropanol, acetone, 1,2-propanediol, n-alkylpyrrolidones (e.g., the Agsolex series), a petroleum based-oil (e.g., aromatic 200) or a mineral oil (e.g., paraffin oil)). In some cases, the nematicidal composition further includes another pesticide (e.g., nematicide, insecticide or fungicide) such as an avermectin (e.g., ivermectin), milbemycin, imidacloprid, aldicarb, oxamyl, fenamiphos, fosthiazate, metam sodium, etridiazole, penta-chloro-nitrobenzene (PCNB), flutolanil, metalaxyl, mefonoxam, and fosetyl-al. Useful fungicides include, but are not limited to, silthiofam, fludioxonil, myclobutanil, azoxystrobin, chlorothalonil, propiconazole, tebuconazole and pyraclostrobin. The composition may also comprise herbicides (e.g., trifloxysulfuron, glyphosate, halosulfuron) and other chemicals for disease control (e.g., chitosan).

Also described is a nematicidal composition comprising: oxazole, oxadiazole or thiadiazole analogs or mixtures of analogs selected from the group consisting of the compounds 3-(4-chlorophenyl)-5-(furan-2-ylmethyl)-1,2,4-oxadiazole, 3-(3-chlorophenyl)-5-(furan-2-ylmethyl)-1,2,4-oxadiazole, 3-(4-chlorophenoxy)-5-(furan-2-yl)-1,2,4-oxadiazole, 3-(3-chlorophenoxy)-5-(furan-2-yl)-1,2,4-oxadiazole, 3-(4-chlorobenzyl)-5-(furan-2-yl)-1,2,4-thiadiazole, 4-(2,4-dichlorophenyl)-2-(furan-2-yl)oxazole, 4-(2,4-dimethylphenyl)-2-(furan-2-yl)oxazole, 4-(4-chlorophenyl)-2-(furan-2-yl)oxazole, 5-(4-chlorophenyl)-2-(thiophen-2-ylthio)oxazole, 5-(4-chlorophenyl)-2-(1H-pyrrol-1-yl)oxazole.

In various embodiments the composition further comprises an aqueous surfactant. Examples of surfactants that can be used include, Span 20, Span 40, Span 80, Span 85, Tween 20, Tween 40, Tween 80, Tween 85, Triton X 100, Makon 10, Igepal CO 630, Brij 35, Brij 97, Tergitol TMN 6, Dowfax 3B2, Physan and Toximul TA 15. In some cases, the nematicidal composition further includes a permeation enhancer (e.g., cyclodextrin). In some cases, the nematicidal composition further includes a co-solvent. Examples of co-solvents that can be used include ethyl lactate, methyl soyate/ethyl lactate co-solvent blends (e.g., Steposol), isopropanol, acetone, 1,2-propanediol, n-alkylpyrrolidones (e.g., the Agsolex series), a petroleum based-oil (e.g., aromatic 200) or a mineral oil (e.g., paraffin oil)). In some cases, the nematicidal composition further includes another pesticide (e.g., nematicide, insecticide or fungicide) such as an avermectin (e.g., ivermectin), milbemycin, imidacloprid, aldicarb, oxamyl, fenamiphos, fosthiazate, metam sodium, etridiazole, penta-chloro-nitrobenzene (PCNB), flutolanil, metalaxyl, mefonoxam, and fosetyl-al. Useful fungicides include, but are not limited to, silthiofam, fludioxonil, myclobutanil, azoxystrobin, chlorothalonil, propiconazole, tebuconazole and pyraclostrobin. The composition may also comprise herbicides (e.g., trifloxysulfuron, glyphosate, halosulfuron) and other chemicals for disease control (e.g., chitosan).

Also described is a method for control of unwanted parasitic nematode (e.g., nematodes other than *C. elegans*), the method including administering to vertebrates, plants, seeds or soil a nematicidal composition including a compound of any of the formulae described herein in any of the nematicidal compositions described herein.

In some instances, the nematode infects plants and the nematicidal composition is applied to the soil or to plants. In some instances, the nematicidal composition is applied to soil before planting. In some instances, the nematicidal composition is applied to soil after planting. In some instances, the nematicidal composition is applied to soil using a drip system. In some instances, the nematicidal composition is applied to soil using a drench system. In some instances, the nematicidal composition is applied to plant roots or plant foliage (e.g., leaves, stems). In some instances the nematicide composition is tilled into the soil or applied in furrow. In some instances, the nematicidal composition is applied to seeds. In some instances, the nematode parasite infects a vertebrate. In some instances, the nematicidal composition is administered to non-human vertebrate. In some instances, the nematicidal composition is administered to a human. In some instances, the nematicidal composition is formulated as a drench to be administered to a non-human animal. In some instances, the nematicidal composition is formulated as an orally administered drug. In some instances, the nematicidal composition is formulated as an injectable drug. In some instances, the nematicidal composition is formulated for topical applications such as pour-ons, or for the use in tags or collars.

Also described herein is a method of treating a disorder (e.g., an infection) caused by a parasitic nematode, (e.g., *M. incognita, H. glycines, B. longicaudatus, H. contortus, A. suum, B. malayi*) in a subject, e.g., a host plant, animal, or person. The method includes administering to the subject an effective amount of a compound having formula I, Ia, II, IIa, IIb, III, IIIa, IIIb, IV, IVa, V, Va, Vb, VI, VIa, VIb, VII, VIIa, VIII, VIIIa, VIIIb, IX, IXa, IXb, X, Xa, XI, XIa, XIb, XII, XIIa, XIIb, XIII, XIIIa, XIV, XIVa, XIVb, XV, XVa, XVb, XVI, XVIa, XVII, XVIIa, XVIIb, XVIII, XVIIIa, XVIIIb, XIX, XIXa, XIXb, XIXc, XIXd, XIXe, XX, XXa, XXb, XXc, XXd or XXe. The compound may be delivered by several means including pre-planting, post-planting and as a feed additive, drench, external application, pill or by injection.

In still another aspect, methods of inhibiting a parasitic nematode (e.g., *M. incognita, H. glycines, B. longicaudatus, H. contortus, A. suum, B. malayi*) are provided. Such methods can include contacting the nematode (at any stage of growth), with a compound, e.g., a compound having Formula I, Ia, II, IIa, IIb, III, IIIa, IIIb, IV, IVa, V, Va, Vb, VI, VIa, VIb, VII, VIIa, VIII, VIIIa, VIIIb, IX, IXa, IXb, X, Xa, XI, XIa, XIb, XII, XIIa, XIIb, XIII, XIIIa, XIV, XIVa, XIVb, XV, XVa, XVb, XVI, XVIa, XVII, XVIIa, XVIIb, XVIII, XVIIIa, XVIIIb, XIX, XIXa, XIXb, XIXc, XIXd, XIXe, XX, XXa, XXb, XXc, XXd or XXe is provided.

In another aspect, methods of reducing the viability or fecundity or slowing the growth or development or inhibiting the infectivity of a nematode using a nematicidal compound, e.g., a compound having Formula I, Ia, II, IIa, IIb, III, IIIa, IIIb, IV, IVa, V, Va, Vb, VI, VIa, VIb, VII, VIIa, VIII, VIIIa, VIIIb, IX, IXa, IXb, X, Xa, XI, XIa, XIb, XII, XIIa, XIIb, XIII, XIIIa, XIV, XIVa, XIVb, XV, XVa, XVb, XVI, XVIa, XVII, XVIIa, XVIIb, XVIII, XVIIIa, XVIIIb, XIX, XIXa, XIXb, XIXc, XIXd, XIXe, XX, XXa, XXb, XXc, XXd or XXe is provided. Such methods can include contacting the nematode with specific a compound, e.g., a compound having Formula I, Ia, II, IIa, IIb, III, IIIa, IIIb, IV, IVa, V, Va, Vb, VI, VIa, VIb, VII, VIIa, VIII, VIIIa, VIIIb, IX, IXa, IXb, X, Xa, XI, XIa, XIb, XII, XIIa, XIIb, XIII, XIIIa, XIV, XIVa, XIVb, XV, XVa, XVb, XVI, XVIa, XVII, XVIIa, XVIIb, XVIII, XVIIIa, XVIIIb, XIX, XIXa, XIXb, XIXc, XIXd, XIXe, XX, XXa, XXb, XXc, XXd or XXe; (c) reducing the viability or fecundity of the nematode parasite.

Also described is a method for reducing the viability, growth, or fecundity of a nematode parasite, the method comprising exposing the nematode to a compound having Formula I, Ia, II, IIa, IIb, III, IIIa, IIIb, IV, IVa, V, Va, Vb, VI, VIa, VIb, VII, VIIa, VIII, VIIIa, VIIIb, IX, IXa, X, Xa, XI, XIa, XIb, XII, XIIa, XIIb, XIII, XIIIa, XIV, XIVa, XIVb, XV, XVa, XVb, XVI, XVIa, XVII, XVIIa, XVIIb, XVIII, XVIIIa, XVIIIb, XIX, XIXa, XIXb, XIXc, XIXd, XIXe, XX, XXa, XXb, XXc, XXd or XXe and a method of protecting a plant from a nematode infection, the method comprising applying to the plant, to the soil, or to seeds of the plant an compound a compound having Formula I, Ia, II, IIa, IIb, III, IIIa, IIIb, IV, IVa, V, Va, Vb, VI, VIa, VIb, VII, VIIa, VIII, VIIIa, VIIIb, IX, IXa, IXb, X, Xa, XI, XIa, XIb, XII, XIIa, XIIb, XIII, XIIIa, XIV, XIVa, XIVb, XV, XVa, XVb, XVI, XVIa, XVII, XVIIa, XVIIb, XVIII, XVIIIa, XVIIIb, XIX, XIXa, XIXb, XIXc, XIXd, XIXe, XX, XXa, XXb, XXc, XXd or XXe.

Also described is a method for protecting a vertebrate (e.g., a bird or a mammal) from a nematode infection, the method comprising administering to the vertebrate a compound having I, Ia, II, IIa, IIb, III, IIIa, IIIb, IV, IVa, V, Va, Vb, VI, VIa, VIb, VII, VIIa, VIII, VIIIa, VIIIb, IX, IXa, IXb, X, Xa, XI, XIa, XIb, XII, XIIa, XIIb, XIII, XIIIa, XIV, XIVa, XIVb, XV, XVa, XVb, XVI, XVIa, XVII, XVIIa, XVIIb, XVIII, XIIIa, XVIIIb, XIX, XIXa, XIXb, XIXc, XIXd, XIXe, XX, XXa, XXb, XXc, XXd or XXe. The bird can be a domesticated fowl (e.g., a chicken, turkey, duck, or goose). The mammal can be a domesticated animal, e.g., a companion animal (e.g., a cat, dog, horse or rabbit) or livestock (e.g., a cow, sheep, pig, goat, alpaca or llama) or can be a human.

Described herein are methods for controlling nematodes parasites by administering a compound described herein. The methods include administering to vertebrates, plants, seeds or soil a nematicidal composition comprising:

(a) an effective amount of a compound or a mixture of compounds having any of the formulae described herein, for example one of the following formulas:

Formulas:

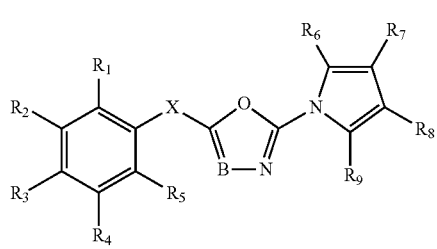

Ia

-continued

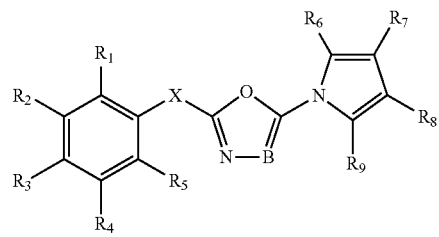

IVa

Formulas:

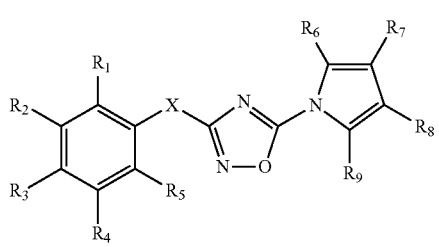

VIIa

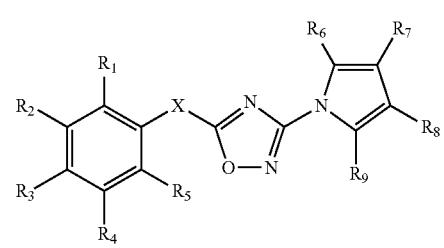

Xa

Formulas:

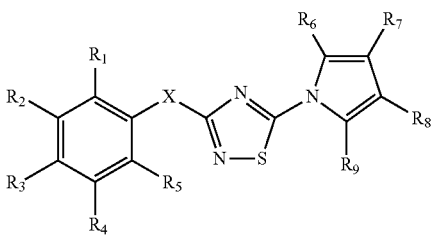

XIIIa

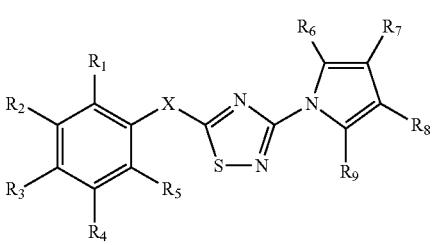

XVIa

Formulas:

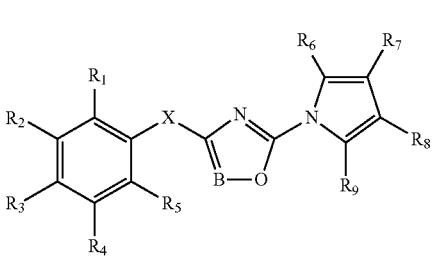

XIXa

-continued

XXa

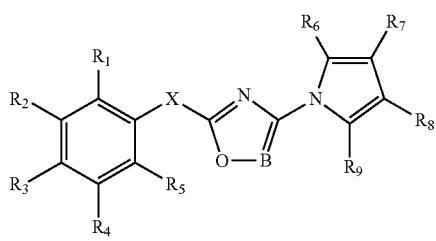

wherein, $R_1$ and $R_5$ are independently selected from hydrogen, $CH_3$, F, Cl, Br, $CF_3$ and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and CO;

$R_6$, $R_7$, $R_8$ and $R_9$ are independently selected from hydrogen, $CH_3$, alkyl, cykloalkyl, heterocyl, and halogen;

B is C(H) or C($CH_3$); and

X is a bond, $CH_2$, O or S.

Formulas:

IIa

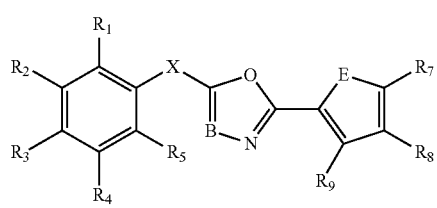

IIb

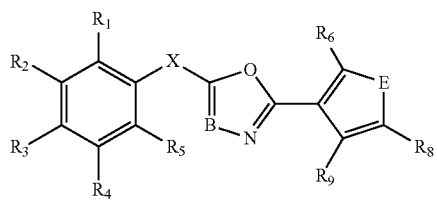

Formulas:

Va

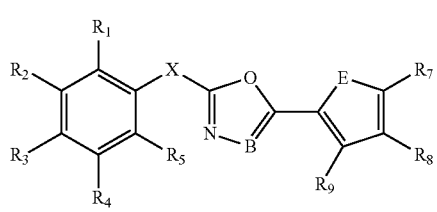

Vb

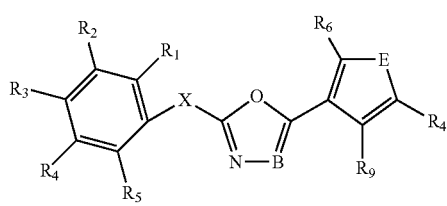

-continued

Formulas:

VIIIa

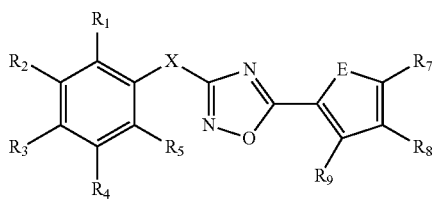

VIIIb

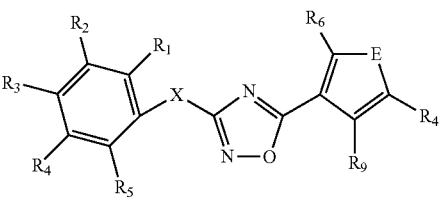

Formulas:

XIa

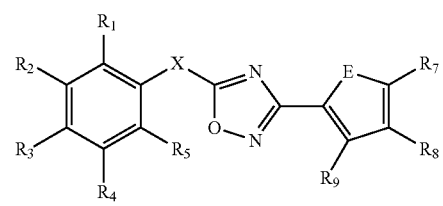

XIb

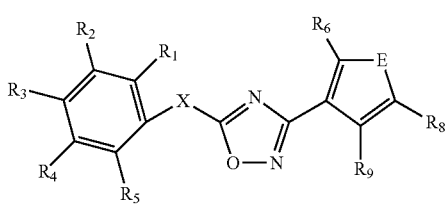

Formulas:

XIVa

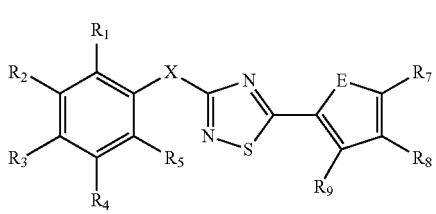

XIVb

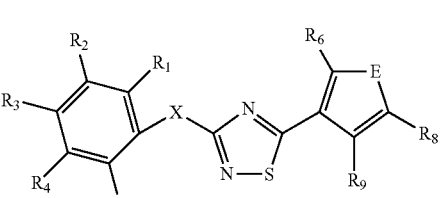

Formulas:

VIIa

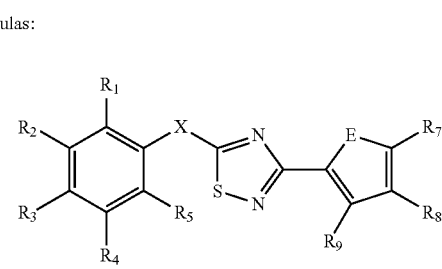

VIIb

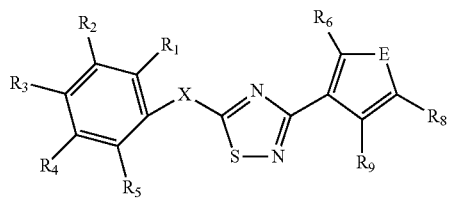

wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, CO;

$R_6$, $R_7$, $R_8$ and $R_9$ are independently selected from hydrogen, F, Cl, $CH_3$, $OCF_3$;

B is C(H), C($CH_3$);

E is O or S; and

X is O or S.

Formulas:

IIIa

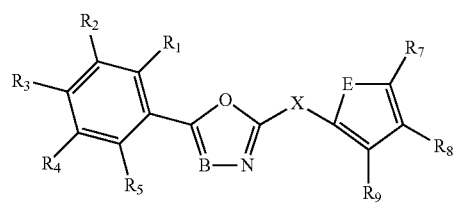

IIIb

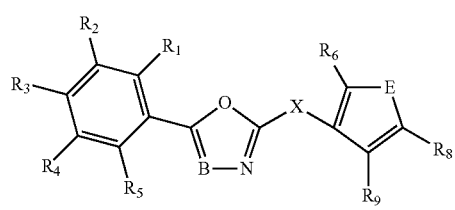

Formulas:

VIa

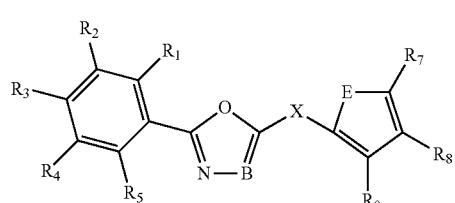

VIb

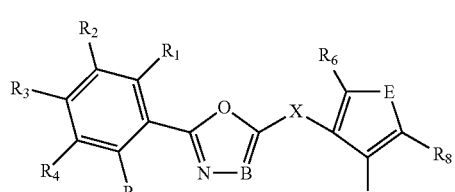

Formulas:

IXa

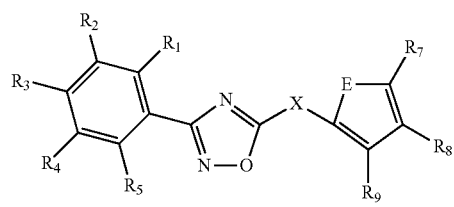

IXb

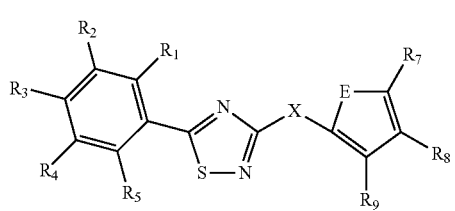

Formulas:

XIIa

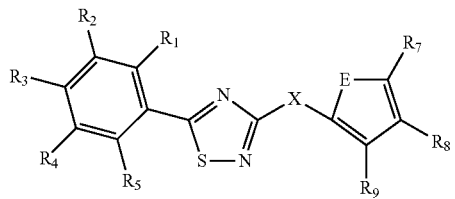

XIIb

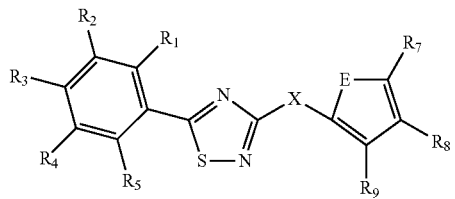

Formulas:

XVa

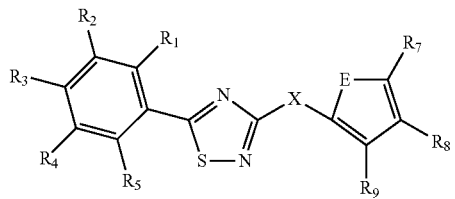

XVb

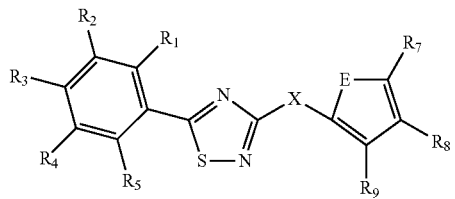

Formulas:

XVIIIa

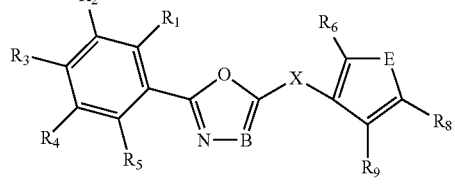

-continued

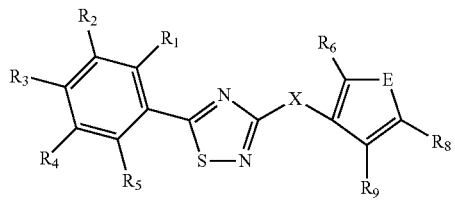
XVIIIb wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, CO;

$R_6$, $R_7$, $R_8$ and $R_9$ are independently selected from hydrogen, F, Cl, $CH_3$, $OCF_3$;

B is C(H), C($CH_3$);

E is O or S; and

X is $CH_2$, O or S.

Formulas:

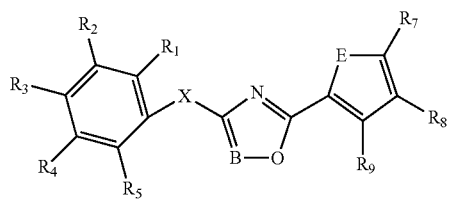
XIXb

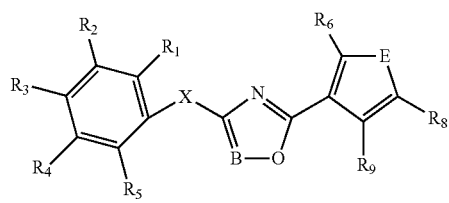
XIXc

Formulas:

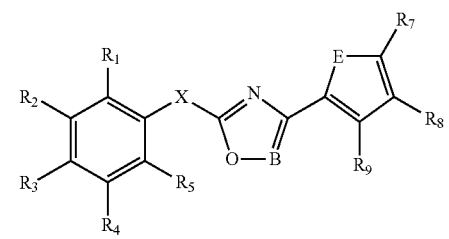
XXb

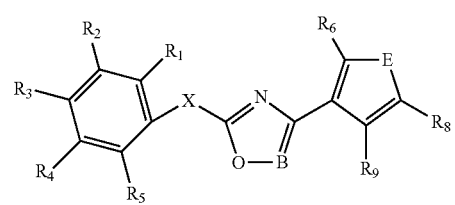
XXc

Formulas:

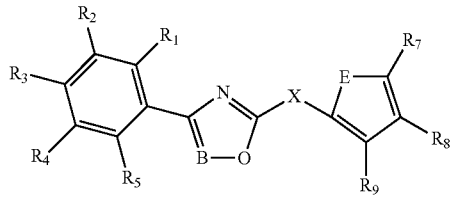
XIXd

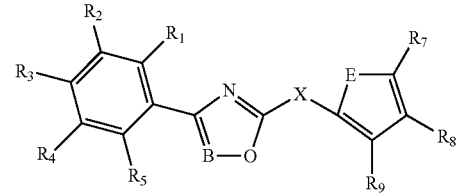
XIXe

Formulas:

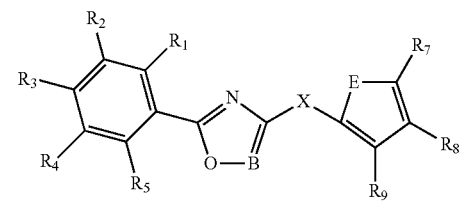
XXd

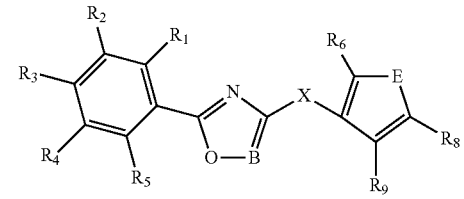
XXe wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, CO;

$R_6$, $R_7$, $R_8$ and $R_9$ are independently selected from hydrogen, F, Cl, $CH_3$, $OCF_3$;

B is C(H) or C($CH_3$);

E is O or S;

X is a bond, $CH_2$, O or S.

The compositions can also include an aqueous surfactant. Examples of surfactants that can be used include, Span 20, Span 40, Span 80, Span 85, Tween 20, Tween 40, Tween 80, Tween 85, Triton X 100, Makon 10, Igepal CO 630, Brij 35, Brij 97, Tergitol TMN 6, Dowfax 3B2, Physan and Toximul TA 15. In some cases, the nematicidal composition further includes a permeation enhancer (e.g., cyclodextrin). In some cases, the nematicidal composition further includes a co-solvent. Examples of co-solvents that can be used include ethyl lactate, methyl soyate/ethyl lactate co-solvent blends (e.g., Steposol), isopropanol, acetone, 1,2-propanediol, n-alkylpyrrolidones (e.g., the Agsolex series), a petroleum based-oil (e.g., aromatic 200) or a mineral oil (e.g., paraffin oil)). In some cases, the nematicidal composition further includes another pesticide (e.g., nematicide, insecticide or fungicide) such as an avermectin (e.g., ivermectin), milbemycin, imidacloprid, aldicarb, oxamyl, fenamiphos, fosthiazate, metam sodium, etridiazole, penta-chloro-nitrobenzene (PCNB), flutolanil, metalaxyl, mefonoxam, and fosetyl-al. Useful fungicides include, but are not limited to, silthiofam, fludioxonil, myclobutanil, azoxystrobin, chlorothalonil, propiconazole, tebuconazole and pyraclostrobin. The composition may also comprise herbicides (e.g., trifloxysulfuron, glyphosate, halosulfuron) and other chemicals for disease control (e.g., chitosan).

Also featured is a method for control of unwanted nematodes comprising administering to vertebrates, plants, seeds or soil a nematicidal composition comprising an effective amount of: (a) a compound selected from the group consisting of 3-(4-chlorophenyl)-5-(furan-2-ylmethyl)-1,2,4-oxadiazole, 3-(3-chlorophenyl)-5-(furan-2-ylmethyl)-1,2,4-oxadiazole, 3-(4-chlorophenoxy)-5-(furan-2-yl)-1,2,4-oxadiazole, 3-(3-chlorophenoxy)-5-(furan-2-yl)-1,2,4-oxadiazole, 3-(4-chlorobenzyl)-5-(furan-2-yl)-1,2,4-thiadiazole, 4-(2,4-dichlorophenyl)-2-(furan-2-yl)oxazole, 4-(2,4-dimethylphenyl)-2-(furan-2-yl)oxazole, 4-(4-chlorophenyl)-2-(furan-2-yl)oxazole, 5-(4-chlorophenyl)-2-(thiophen-2-ylthio)oxazole, 5-(4-chlorophenyl)-2-(1H-pyrrol-1-yl)oxazole.

Also featured is a method for control of unwanted nematodes comprising administering to vertebrates a nematicidal composition comprising an effective amount of: (a) a compound selected from the group consisting of 3-(4-chlorophenyl)-5-(furan-2-ylmethyl)-1,2,4-oxadiazole, 3-(3-chlorophenyl)-5-(furan-2-ylmethyl)-1,2,4-oxadiazole, 3-(4-chlorophenoxy)-5-(furan-2-yl)-1,2,4-oxadiazole, 3-(3-chlorophenoxy)-5-(furan-2-yl)-1,2,4-oxadiazole, 3-(4-chlorobenzyl)-5-(furan-2-yl)-1,2,4-thiadiazole, 4-(2,4-dichlorophenyl)-2-(furan-2-yl)oxazole, 4-(2,4-dimethylphenyl)-2-(furan-2-yl)oxazole, 4-(4-chlorophenyl)-2-(furan-2-yl)oxazole, 5-(4-chlorophenyl)-2-(thiophen-2-ylthio)oxazole, 5-(4-chlorophenyl)-2-(1H-pyrrol-1-yl)oxazole.

In certain embodiments of the method the composition further comprises an aqueous surfactant. Examples of surfactants that can be used include, Span 20, Span 40, Span 80, Span 85, Tween 20, Tween 40, Tween 80, Tween 85, Triton X 100, Makon 10, Igepal CO 630, Brij 35, Brij 97, Tergitol TMN 6, Dowfax 3B2, Physan and Toximul TA 15. In some cases, the nematicidal composition further includes a permeation enhancer (e.g., cyclodextrin). In some cases, the nematicidal composition further includes a co-solvent. Examples of co-solvents that can be used include ethyl lactate, methyl soyate/ethyl lactate co-solvent blends (e.g., Steposol), isopropanol, acetone, 1,2-propanediol, n-alkylpyrrolidones (e.g., the Agsolex series), a petroleum based-oil (e.g., aromatic 200) or a mineral oil (e.g., paraffin oil)). In some cases, the nematicidal composition further includes another pesticide (e.g., nematicide, insecticide or fungicide) such as an avermectin (e.g., ivermectin), milbemycin, imidacloprid, aldicarb, oxamyl, fenamiphos, fosthiazate, metam sodium, etridiazole, penta-chloro-nitrobenzene (PCNB), flutolanil, metalaxyl, mefonoxam, and fosetyl-al. Useful fungicides include, but are not limited to, silthiofam, fludioxonil, myclobutanil, azoxystrobin, chlorothalonil, propiconazole, tebuconazole and pyraclostrobin. The composition may also comprise herbicides (e.g., trifloxysulfuron, glyphosate, halosulfuron) and other chemicals for disease control (e.g., chitosan); the nematode infects plants and the nematicidal composition is applied to the soil or to plants; the nematicidal composition is applied to soil before planting; the nematicidal composition is applied to soil after planting; the nematicidal composition is applied to soil using a drip system; the nematicidal composition is applied to soil using a drench system; the nematicidal composition is applied to plant roots; the pesticidal composition is applied to seeds; the nematicidal composition is applied to the foliage of plants; the nematode infects a vertebrate; the nematicidal composition is administered to a bird or non-human mammal; the nematicidal composition is administered to a human; the nematicidal composition is formulated as a drench to be administered to a non-human animal; the nematicidal composition is formulated as an orally administered drug; and the nematicidal composition is formulated as an injectable drug.

The methods described hereon are particularly valuable for the control nematodes attacking the roots of desired crop plants, ornamental plants, and turf grasses. The desired crop plants can be, for example, soybeans, cotton, corn, tobacco, wheat, strawberries, tomatoes, banana, sugar cane, sugar beet, potatoes, or citrus.

Also described is a nematicidal feed for a non-human vertebrate including:

(a) a feed; and (b) a nematicidal composition, including a nematicidal composition described herein.

In some instances, the feed is selected from the group consisting of: soy, wheat, corn, sorghum, millet, alfalfa, clover, and rye.

Also described are feeds that have been supplemented to include one or more of the compounds described herein.

A nematicidal feed for a non-human vertebrate can comprise: (a) an animal feed; and (b) an effective amount of a nematicidal compound or mixtures of compounds having any of the formulae described herein, for example having one of the formula below:

Formulas:

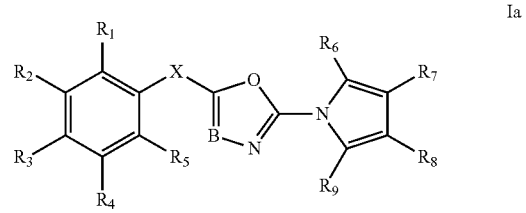

Ia

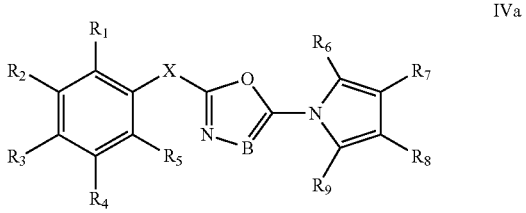

IVa

Formulas:

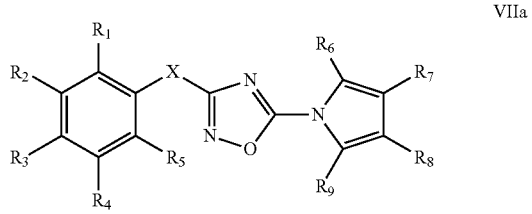

VIIa

-continued

Xa
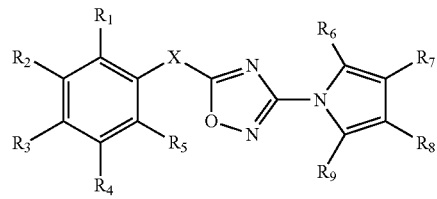

Formulas:

XIIIa
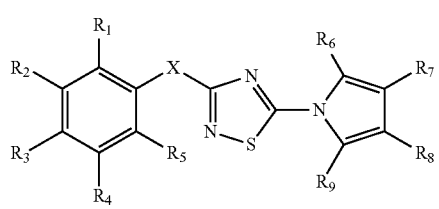

XVIa
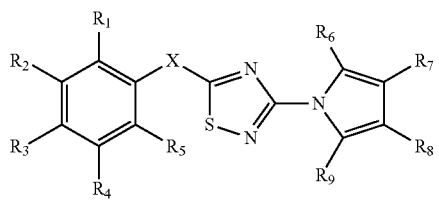

Formulas:

XIXa
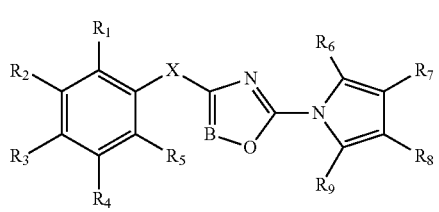

XXa
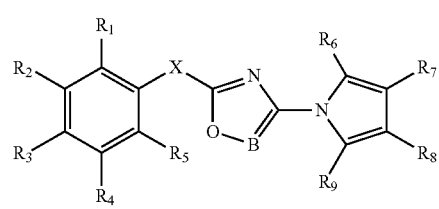

wherein,
R₁ and R₅ are independently selected from hydrogen, CH₃, F, Cl, Br, CF₃ and OCF₃;
R₂ and R₄ are independently selected from hydrogen, F, Cl, Br, and CF₃;
R₃ is selected from hydrogen, CH₃, CF₃, F, Cl, Br, OCF₃, OCH₃, CN, and CO;
R₆, R₇, R₈ and R₉ are independently selected from hydrogen, CH₃, alkyl, cykloalkyl, heterocyl, and halogen;
B is C(H) or C(CH₃); and
X is a bond, CH₂, O or S.

Formulas:

IIa
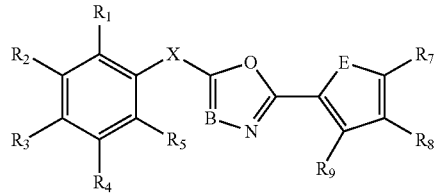

IIb
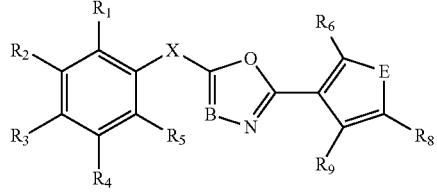

Formulas:

Va
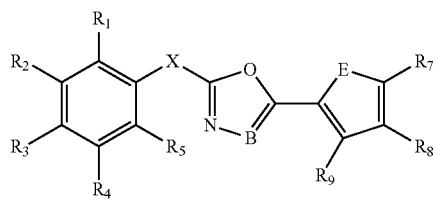

Vb
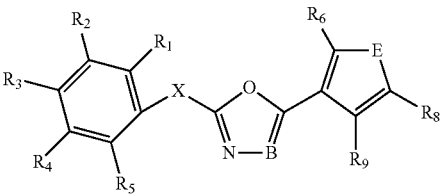

Formulas:

VIIIa
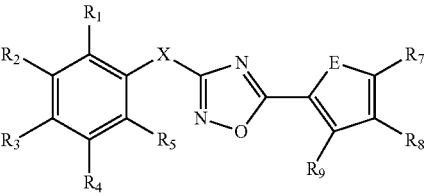

VIIIb
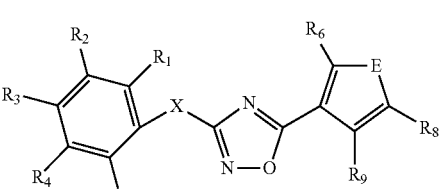

Formulas:

XIa
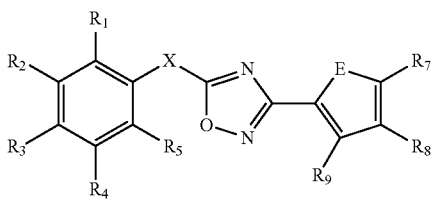

-continued

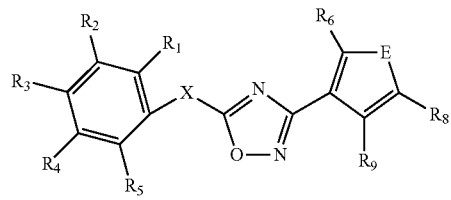
XIb

Formulas:

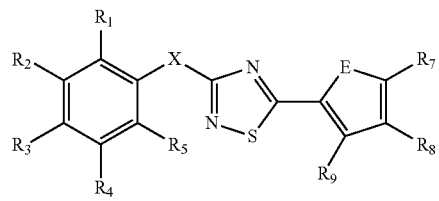
XIVa

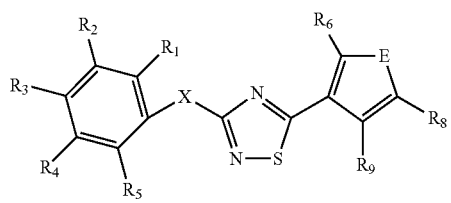
XIVb

Formulas:

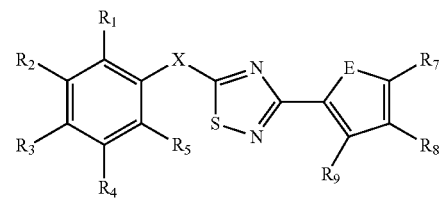
VIIa

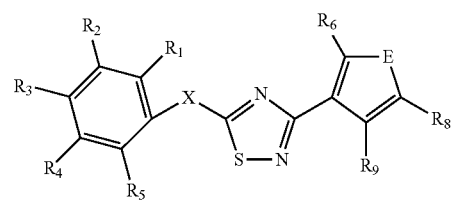
VIIb wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, CO;

$R_6$, $R_7$, $R_8$ and $R_9$ are independently selected from hydrogen, F, Cl, $CH_3$, $OCF_3$;

B is C(H), C($CH_3$);

E is O or S; and

X is O or S.

Formulas:

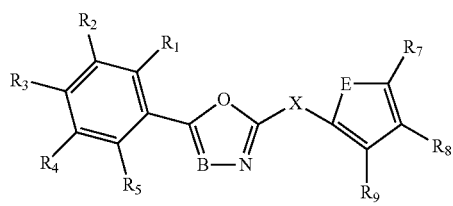
IIIa

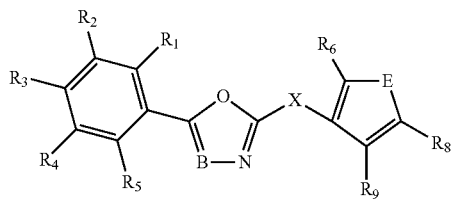
IIIb

Formulas:

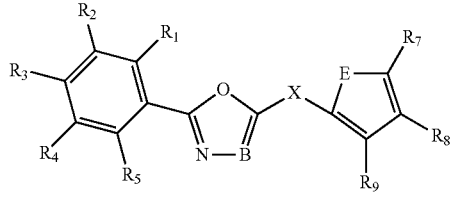
VIa

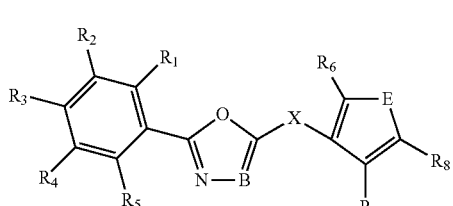
VIb

Formulas:

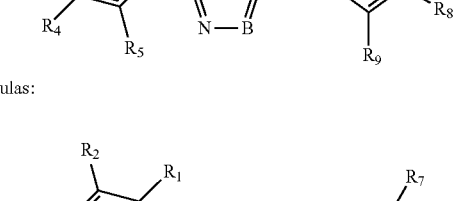
IXa

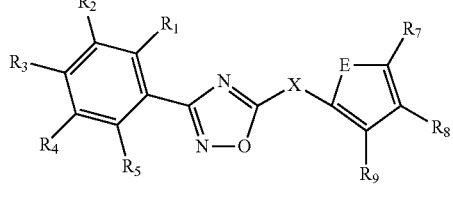
IXb

Formulas:

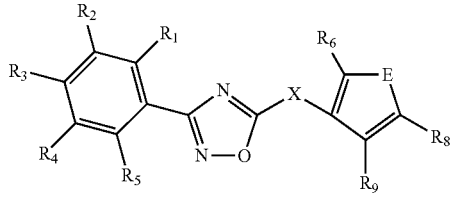
XIIa

XIIb

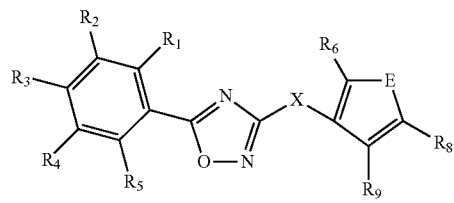

Formulas:

XVa

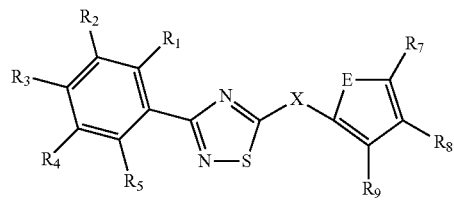

XVb

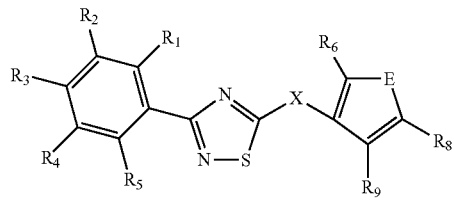

Formulas:

XVIIIa

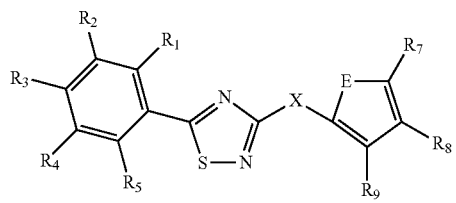

XVIIIb

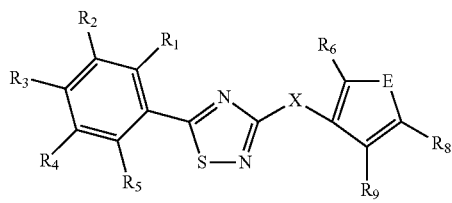

wherein,
R$_1$ and R$_5$ are independently selected from hydrogen, CH$_3$, F, Cl, Br, CF$_3$, OCF$_3$;
R$_2$ and R$_4$ are independently selected from hydrogen, F, Cl, Br, CF$_3$;
R$_3$ is selected from hydrogen, CH$_3$, CF$_3$, F, Cl, Br, OCF$_3$, OCH$_3$, CN, CO;
R$_6$, R$_7$, R$_8$ and R$_9$ are independently selected from hydrogen, F, Cl, CH$_3$, OCF$_3$;
B is C(H), C(CH$_3$);
E is O or S; and
X is CH$_2$, O or S.

Formulas:

XIXb

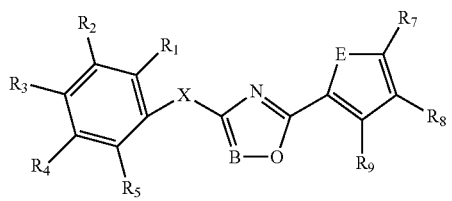

XIXc

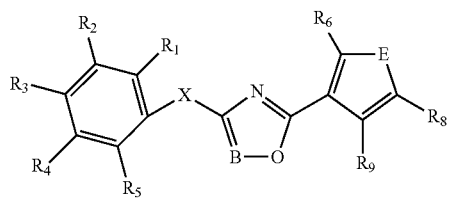

Formulas:

XXb

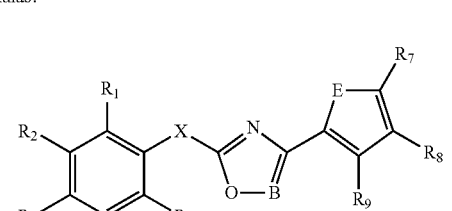

XXc

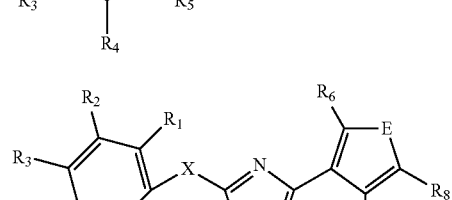

Formulas:

XIXd

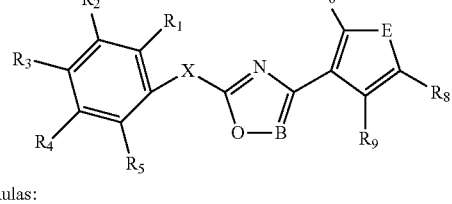

XIXe

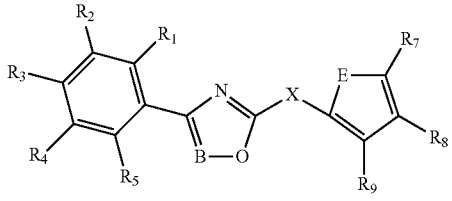

Formulas:

XXd

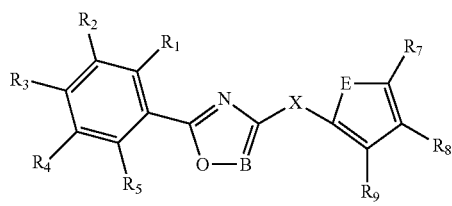

-continued

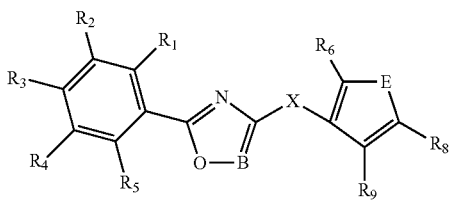

XXe wherein, $R_1$ and $R_5$ are independently selected from hydrogen, $CH_3$, F, Cl, Br, $CF_3$, $OCF_3$;

$R_2$ and $R_4$ are independently selected from hydrogen, F, Cl, Br, $CF_3$;

$R_3$ is selected from hydrogen, $CH_3$, $CF_3$, F, Cl, Br, $OCF_3$, $OCH_3$, CN, CO;

$R_6$, $R_7$, $R_8$ and $R_9$ are independently selected from hydrogen, F, Cl, $CH_3$, $OCF_3$;

B is C(H) or C($CH_3$);

E is O or S;

X is a bond, $CH_2$, O or S.

The feed can be selected from the group consisting of: soy, wheat, corn, sorghum, millet, alfalfa, clover, and rye.

As used herein, an agent with "anthelmintic or anthelminthic or antihelminthic activity" is an agent, which when tested, has measurable nematode-killing activity or results in reduced fertility or sterility in the nematodes such that fewer viable or no offspring result, or compromises the ability of the nematode to infect or reproduce in its host, or interferes with the growth or development of a nematode. The agent may also display nematode repellant properties. In the assay, the agent is combined with nematodes, e.g., in a well of microtiter dish, in liquid or solid media or in the soil containing the agent. Staged nematodes are placed on the media. The time of survival, viability of offspring, and/or the movement of the nematodes are measured. An agent with "anthelmintic or anthelminthic or antihelmthic activity" can, for example, reduce the survival time of adult nematodes relative to unexposed similarly staged adults, e.g., by about 20%, 40%, 60%, 80%, or more. In the alternative, an agent with "anthelmintic or anthelminthic or antihelminthic activity" may also cause the nematodes to cease replicating, regenerating, and/or producing viable progeny, e.g., by about 20%, 40%, 60%, 80%, or more. The effect may be apparent immediately or in successive generations.

The term "halo" or "halogen" refers to any radical of fluorine, chlorine, bromine or iodine.

The term "alkyl" as employed herein by itself or as part of another group refers to both straight and branched chain radicals of up to ten carbons. Typical C1-10 alkyl groups include methyl, ethyl, propyl, isopropyl, butyl, sec-butyl, tert-butyl, 3-pentyl, hexyl and octyl groups, which may be optionally substituted.

The term "alkenyl" as employed herein by itself or as part of another group means a straight or branched chain radical of 2-10 carbon atoms, unless the chain length is limited thereto, including at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

Alkoxy groups contain oxygen substituted by one of the C1-10 alkyl groups mentioned above, which may be optionally substituted.

Alkylthio groups contain sulfur substituted by one of the C1-10 alkyl groups mentioned above, which may be optionally substituted. Also included are the sulfoxides and sulfones of such alkylthio groups.

Amino groups include —NH2, —$NHR_{15}$ and —$NR_{15}R_{16}$, wherein $R_{15}$ and $R_{16}$ are C1-10 alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group may be optionally substituted.

The term "aryl" as employed herein by itself or as part of another group refers to monocyclic, bicyclic or tricyclic aromatic groups containing from 6 to 14 carbons in the ring.

Common aryl groups include C6-14 aryl, preferably C6-10 aryl. Typical C6-14 aryl groups include phenyl, naphthyl, phenanthrenyl, anthracenyl, indenyl, azulenyl, biphenyl, biphenylenyl and fluorenyl groups.

Cycloalkyl groups are C3-8 cycloalkyl. Typical cycloalkyl groups include cyclopropyl, cyclobutyl, cyclopentyl, cyclohexyl and cycloheptyl.

The term "arylalkyl" is used herein to mean any of the above-mentioned C1-10 alkyl groups substituted by any of the above-mentioned C6-14 aryl groups. Preferably the arylalkyl group is benzyl, phenethyl or naphthylmethyl. Preferred arylalkyl groups are arylC1alkyl and arylC2alkyl.

The term "arylalkenyl" is used herein to mean any of the above-mentioned C2-10 alkenyl groups substituted by any of the above-mentioned C6-14 aryl groups.

The term "arylalkynyl" is used herein to mean any of the above-mentioned C2-10 alkynyl groups substituted by any of the above-mentioned C6-14 aryl groups.

The term "aryloxy" is used herein to mean oxygen substituted by one of the above-mentioned C6-14 aryl groups, which may be optionally substituted. Common aryloxy groups include phenoxy and 4-methylphenoxy.

The term "arylalkoxy" is used herein to mean any of the above mentioned C1-10 alkoxy groups substituted by any of the above-mentioned aryl groups, which may be optionally substituted. Example arylalkoxy groups include benzyloxy and phenethyloxy.

Example haloalkyl groups include C1-10 alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Acylamino(acylamido) groups include any C1-6 acyl(alkanoyl) attached to an amino nitrogen, e.g., acetamido, chloroacetamido, propionamido, butanoylamido, pentanoylamido and hexanoylamido, as well as aryl-substituted C1-6 acylamino groups, e.g., benzoylamido, and pentafluorobenzoylamido.

Common acyloxy groups are any C1-6 acyl(alkanoyl) attached to an oxy (—O—) group, e.g., formyloxy, acetoxy, propionoyloxy, butanoyloxy, pentanoyloxy and hexanoyloxy.

The term heterocycle is used herein to mean a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable.

Common saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

The term "heteroaryl" as employed herein refers to groups having 5 to 14 ring atoms; 6, 10 or 14π electrons shared in a cyclic array; and containing carbon atoms and 1, 2 or 3 oxygen, nitrogen or sulfur heteroatoms.

Example heteroaryl groups include thienyl (thiophenyl), benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, including without limitation 2H-pyrrolyl, imidazolyl, pyrazolyl, pyridyl(pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-α]pyrimidin-4-one, pyrazolo[1,5-α]pyrimidinyl, including without limitation pyrazolo[1,5-α]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned C1-10 alkoxy groups substituted by any of the above-mentioned heteroaryl groups, which may be optionally substituted.

A preferred pyrrolalkyl is pyrrol C1 alkyl.

Preferred furanlalkyl, thienylalkyl, oxazolyalkyl and isoxazolylalkyl groups are furanlC1alkyl, thienylC1alkyl, oxazolyC1alkyl and isoxazolylC1alkyl respectively.

A permeation enhancer is generally an agent that facilitates the active compounds of the invention.

A co-solvent (i.e., a latent solvent or indirect solvent) is an agent that becomes an effective solvent in the presence of an active solvent and can improve the properties of the primary (active) solvent.

The composition can be produced in concentrated form that includes little or no water. The composition can be diluted with water or some other solvent prior to use to treat plants, seeds, soil or vertebrates.

The details of one or more embodiments of the invention are set forth in the accompanying drawings and the description below. Other features, objects, and advantages of the invention will be apparent from the description and drawings, and from the claims.

DETAILED DESCRIPTION

Described herein are certain compounds, some of which are oxazole, oxadiazole and thiadiazole analogs with potent broad spectrum nematicidal activity.

The nematicidal compounds may be supplied to plants exogenously, through sprays for example. These compounds may also be applied as a seed coat. The compounds can be applied to plants or the environment of plants needing nematode control, or to animals or the food of animals needing nematode parasite control. The compositions may be applied by, for example drench or drip techniques. With drip applications compounds can be applied directly to the base of the plants or the soil immediately adjacent to the plants. The composition may be applied through existing drip irrigation systems. This procedure is particularly applicable for cotton, strawberries, tomatoes, potatoes, vegetables and ornamental plants. Alternatively, a drench application can be used where a sufficient quantity of nematicidal composition is applied such that it drains to the root area of the plants. The drench technique can be used for a variety of crops and turf grasses. The drench technique can also be used for animals. Preferably, the nematicidal compositions would be administered orally to promote activity against internal parasitic nematodes. Nematicidal compositions may also be administered in some cases by injection of the host animal or by topical applications.

The concentration of the nematicidal composition should be sufficient to control the parasite without causing significant phytotoxicity to the desired plant or undue toxicity to the animal host. The compounds disclosed in this invention have a good therapeutic window.

We have surprisingly found that certain oxazole, oxadiazole and thiadiazole analogs (e.g., 3-(4-chlorophenyl)-5-(furan-2-ylmethyl)-1,2,4-oxadiazole, 3-(3-chlorophenyl)-5-(furan-2-ylmethyl)-1,2,4-oxadiazole, 3-(4-chlorophenoxy)-5-(furan-2-yl)-1,2,4-oxadiazole, 3-(3-chlorophenoxy)-5-(furan-2-yl)-1,2,4-oxadiazole, 3-(4-chlorobenzyl)-5-(furan-2-yl)-1,2,4-thiadiazole, 4-(2,4-dichlorophenyl)-2-(furan-2-yl)oxazole, 4-(2,4-dimethylphenyl)-2-(furan-2-yl)oxazole, 4-(4-chlorophenyl)-2-(furan-2-yl)oxazole, 5-(4-chlorophenyl)-2-(thiophen-2-ylthio)oxazole, 5-(4-chlorophenyl)-2-(1H-pyrrol-1-yl)oxazole) have nematicidal potencies comparable with organophosphate and carbamate standards yet display excellent selectivity for nematodes over plants and animals. Thus, these analogs will provide useful compounds for nematode parasite control.

The nematicidal agents described herein can be applied in conjunction with another pesticidal agents. The second agent may, for example, be applied simultaneously or sequentially. Such pesticidal agents can include for example, avermectins for animal applications.

The aforementioned nematicidal compositions can be used to treat diseases or infestations caused by nematodes of the following non-limiting, exemplary genera: *Anguina, Ditylenchus, Tylenchorhynchus, Pratylenchus, Radopholus, Hirschmanniella, Nacobbus, Hoplolaimus, Scutellonema, Rotylenchus, Helicotylenchus, Rotylenchulus, Belonolaimus, Heterodera*, other cyst nematodes, *Meloidogyne, Criconemoides, Hemicycliophora, Paratylenchus, Tylenchulus, Aphelenchoides, Bursaphelenchus, Rhadinaphelenchus, Longidorus, Xiphinema, Trichodorus*, and *Paratrichodorus, Dirofiliaria, Onchocerca, Brugia, Acanthocheilonema, Aelurostrongylus, Ancylostoma, Angiostrongylus, Ascaris, Bunostomum, Capillaria, Chabertia, Cooperia, Crenosoma, Dictyocaulus, Dioctophyme, Dipetalonema, Dracunculus, Enterobius, Filaroides, Haemonchus, Lagochilascaris, Loa, Manseonella, Muellerius, Necator, Nematodirus, Oesophagostomum, Ostertagia, Parafilaria, Parascaris, Physaloptera, Protostrongylus, Setaria, Spirocerca, Stephanogilaria, Strongyloides, Strongylus, Thelazia, Toxascaris, Toxocara, Trichinella, Trichostrongylus, Trichuris, Unci-* naria, and *Wuchereria*. Particularly preferred are nematodes including *Dirofilaria, Onchocerca, Brugia, Acanthocheilonema, Dipetalonema, Loa, Mansonella, Parafilaria, Setaria, Stephanofilaria,* and *Wucheria, Pratylenchus, Heterodera, Meloidogyne, Paratylenchus*. Species that are particularly preferred are: *Ancylostoma caninum, Haemonchus contortus, Trichinella spiralis, Trichurs muris, Dirofilaria immitis, Dirofilaria tenuis, Dirofilaria repens, Dirofilari ursi, Ascaris suum, Toxocara canis, Toxocara cati, Strongyloides ratti, Parastrongyloides trichosuri, Heterodera glycines, Globodera pallida, Meloidogyne javanica, Meloidogyne incognita,* and *Meloidogyne arenaria, Radopholus similis, Longidorus elongatus, Meloidogyne hapla,* and *Pratylenchus penetrans*.

The following examples are, therefore, to be construed as merely illustrative, and not limitative of the remainder of the disclosure in any way whatsoever. All of the publications cited herein are hereby incorporated by reference in their entirety.

EXAMPLES

Example 1

*M. Incognita* Testing of Several Nematicidal Compounds in a Miniaturized Greenhouse Assay Overview:

The test compound is dissolved in an acetone solution and added to water. A sprouted cucumber seedling is placed into a vial with dry sand and the water-chemical solution is added immediately. Twenty four hours later *Meloidogyne incognita* eggs are added to the vials and 10 to 12 days later the roots are evaluated for nematode galling.

Procedure:

Cucumber seeds are sprouted for 3 days in moist paper towels. Acceptable sprouts should be 3 to 4 cm long with several lateral roots just emerging. Stock solutions of chemistry are prepared in a mixture of acetone and Triton X100 (412 mg in 500 mL) to a final concentration of 5 mg/mL. The chemical stock solution is then added to 10 mL deionized water plus 0.015% Triton X100 and mixed thoroughly. This is enough to test each condition in triplicate. Ten mL dry sand is added to each vial. At this time the solubility of the chemistry is visually determined and recorded as either ppt (large precipitates) or cloudy (fine precipitates). Seedlings are planted by tilting the vial and laying the seedling in the correct orientation so that the cotyledons are just above the sand and then tilting back to cover the radicles with sand. 3.3 ml water/chemical mix is added to each vial and the vials placed in racks under fluorescent light banks. The vials are inoculated two days after planting by adding 500 vermiform *M. incognita* eggs to each vial in 50 uL of deionized or spring water. The vials are then kept under the fluorescent lamps at ambient room temperature and watered as needed with 1 mL deionized water, usually twice during duration of test. Harvest of the cucumber plants is done 10 to 12 days after inoculation by washing sand off the roots. A root gall rating and visual phytotoxicity rating is assigned using the following scales: Gall rating scale (Gall: % root mass galled): 0=0-5%; 1=6-20%; 2=21-50%; and 3=51-100%. The average of the triplicate gall rating is then calculated: green=0.00-0.33 (no galls); yellow=0.67-1.33 (mild galling); orange=1.67-2.33 (moderate galling); red=2.67-3.00 (severe galling). Visual phytotoxicity scale is also assigned (Vis. tox; visual reduction in root mass compared to the control): rs1=mild stunting; rs2=moderate stunting; rs3=severe stunting.

TABLE 1A

Potent nematicidal oxadiazole, thiadiazole and oxazole 2-thiophene and 2-furan analogs showing examples of substitutions compatible with high activity

| Name | Analog | 8 ppm gall ratings |
|---|---|---|
| 1 | 4-Cl-C6H4-oxadiazole-CH2-furan | 1.3[a] |
| 2 | 3-Cl-C6H4-oxadiazole-CH2-furan | 1.3[a] |
| 3 | 4-Cl-C6H4-O-oxadiazole-furan | 0[b] |
| 4 | 3-Cl-C6H4-O-oxadiazole-furan | 0[b] |
| 5 | 4-Cl-C6H4-CH2-thiadiazole-furan | 0.67[b] |
| 6 | 2,4-diCl-C6H3-oxazole-furan | 0.33[c] |
| 7 | 2,4-diMe-C6H3-oxazole-furan | 1.33[c] |
| 8 | 4-Cl-C6H4-oxazole-furan | 0.67[d] |

TABLE 1A-continued

Potent nematicidal oxadiazole, thiadiazole and oxazole 2-thiophene and 2-furan analogs showing examples of substitutions compatible with high activity

| Name | Analog | 8 ppm gall ratings |
|---|---|---|
| 9 | 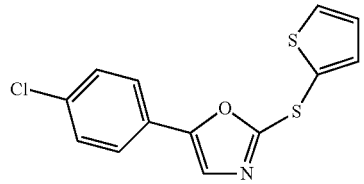 [SMILES: Clc1ccc(-c2cnc(Sc3cccs3)o2)cc1] | 1.33[d] |
| Oxamyl (1 ppm) | | 1.33[a], 1.33[b], 1.33[c], 1.33[d] |

*Data with the same letters are taken from the same test.

A variety of single or double substitutions on the six membered aromatic ring of the phenyl-2-furan and phenyl-2-thiophene oxadiazoles and oxazoles are compatible with high nematicidal activity. Examples of preferred single substitutions include but are not limited to halogens, $CH_3$, $CF_3$, $OCF_3$ and $OCH_3$ especially in the para position (4-position) of the phenyl ring. The phenyl ring can also be multiply substituted in a way compatible with high nematicidal efficacy. Ring numbering system is shown below.

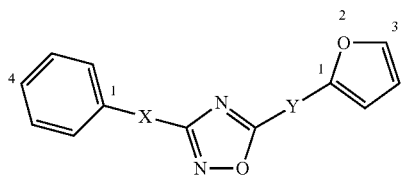

TABLE 1B

A potent nematicidal oxazole pyrole analogs showing example showing high nematicidal activity

| Name | Analog | 1 ppm gall ratings* |
|---|---|---|
| 10 | 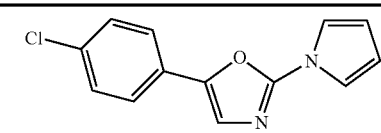 | 1.33 |
| Oxamyl | | 1.33[e] |
| Fenamiphos | | 0 |

The phenyl-N-pyrrole analog has nematicidal potency equivalent to the commercial carbamate nematicide oxamyl and similar to the nematicide fenamiphos. Oxamyl and fenamiphos are highly toxic compounds classified as toxicity Class I chemicals by the US Environmental Protection Agency.

Example 2

General Greenhouse Testing Protocols

Soybean Planting and Growth:

Soybeans seeds are planted in 100% sand in two inch square plastic pots. Chemical treatment is done when the soybeans show the first trifoliate beginning to emerge about 10 to 12 days after planting. At least four hours after chemical application the nematode soybean cyst nematode (SCN) eggs are applied and 28 days after the egg inoculation the test is harvested.

Cucumber Planting and Growth

Cucumber seeds are planted in a sandy soil mixture in two inch square plastic pots. When the cotyledons are fully opened and just as the first leaf begins to emerge, usually 7 days after planting, chemistry for the 7-day treatment is applied. One week later the chemistry for the 0 day treatment is applied. Separate plants are used for each application. The plants are generally in the 1-2 leaf stage now. At least four hours after the chemistry application the pots are inoculated with root knot nematode (RKN) eggs. Plants are rated for galling 14 days after the egg inoculation.

Chemical Formulation and Application

One milligram of chemistry per four pots is equal to one kilogram per hectare of chemical. A standard test uses four replications. For rates above 2 kg/ha, the desired amount of chemical is weighed into a 30 ml vial (example: 8 kg/ha rate=8 mg chemical in 30 ml vial). The chemical is dissolved in 2 ml of appropriate solvent, generally acetone. For rates below 2 kg/ha, 2 milligrams of chemistry is weighed into the vial and dissolved in 2 ml of the solvent. The appropriate amount of chemical concentrate is then pipetted into a separate 30 ml vial and solvent is added to bring the volume to 2 ml (example 0.5 kg/ha=0.5 ml of concentrate+1.5 ml solvent). Each dissolved concentrate is then brought to a total of 20 milliliters using 0.05% Triton X 100 surfactant solution.

Chemical and Nematode Application

Pots to be treated are moist but not saturated. To each of four pots, five milliliters of the appropriate chemical solution is pipetted to the media surface making sure to avoid contact with the base of the plant. Immediately following chemical application, using a mist nozzle, the pot surface is wetted sufficiently to saturate the pot watering in the chemistry. The chemical application is done in the morning.

Nematode eggs, either SCN or RKN, are added to distilled water to create a concentration of 1000 vermiform eggs per liter of water. At least four hours after chemical treatment the eggs are applied to the treated pots plus non-treated check plants. A small hole about 1 cm deep is punched into the pot surface. One milliliter of the nematode egg slurry is pipetted into the hole. Immediately afterwards the hole is gently covered. Watering of the test plants is then restricted to only water as needed to prevent wilt for a period of 24 hours. After the 24 hour restricted watering, normal sub-irrigation watering is done for the duration of the test.

TABLE 2A

RKN greenhouse soil assay on cucumber plants

| Name | Analog | 0 day 1 kg/ha rate* |
|---|---|---|
| 3 | [4-Cl-phenyl-O-oxadiazole-furan structure] | 89% |
| 10 | [Cl-phenyl-oxazole-pyrrole structure] | 100% |
| 4 | [3-Cl-phenyl-O-oxadiazole-furan structure] | 83% |
| Fenamiphos | | 100% |

*Data shows percent control (i.e., galling reduction) relative to the control blank treatment. Data with the same letters are taken from the same test.

TABLE 2B

SCN greenhouse soil assay on soybean plants

| Name | Analog | 0 day 0.25 kg/ha rate* |
|---|---|---|
| 3 | [4-Cl-phenyl-O-oxadiazole-furan structure] | 79%$^a$, 79%$^b$ |
| 4 | [3-Cl-phenyl-O-oxadiazole-furan structure] | 67%$^a$, 78%$^b$ |
| Oxamyl | | 67%$^b$ |
| Fenamiphos | | 90%$^a$ |

*Data shows percent control (i.e., cyst reduction) relative to the control blank treatment. Data with the same letters are taken from the same test.

Certain oxazoles, oxadiazoles and thiadiazoles are highly efficacious nematicides in bioactive soil with potencies comparable to fenamiphos and oxamyl.

Example 3

*Belonalaimus Longicaudatus* (Sting Nematode) Testing Protocols

Populations of sting (*Belonolaimus longicaudatus*) nematodes are maintained on St. Augustine turf grass on soil in 15-cm pots. At test initiation the turf is removed from the pots and the soil containing nematode eggs, juveniles, and adults is subdivided into pots each containing a volume of 125 cm$^3$. The compounds to be tested are dissolved in 3 ml of acetone using 3, 6, or 15 mg to achieve equivalent surface area application rates of 2, 4, or 10 kg/ha, respectively. The 3 ml acetone stock solution is added to 30 ml of water, and 5 ml of that solution is used to drench each of 6 replicate test pots prepared as described above. The treated pots containing nematodes are incubated in the laboratory at ambient temperature of approximately 25° C. After 3 days the soil from each pot is washed onto a modified Baermann apparatus comprised of a screen supporting a layer of filter paper on which the soil sample is placed and set in a dish of water. The samples are then incubated at 25° C. for 24 hours to allow the live nematodes to migrate through the paper and screen and into a water reservoir to be collected for counting with a light microscope. Nematodes that have been killed or immobilized by the test compounds are not able to migrate into the reservoir.

Example 4

*C. Elegans* Testing Protocols

Various compounds were tested for nematicidal activity against *C. elegans* using contact assays in wells. The assays were performed as described below. The test compounds were solubilized in DMSO at 10 mg/ml to create 100× stock solutions. A dilution series was created by diluting the stock solution with DMSO. For each well assay 4 ul of the appropriate dilution is added to a well of a test plate.

A 400 ul aliquot of bacterial stock (in M9 buffer with ampicillin and nystatin) are added to each well of the test plate. Worms are added and the test plate placed on a rotary shaker and held at 20° C. Worms are examined and scored at 4 hrs, 24 hrs, 48 hrs and 72 hours.

L1 worms and L4 worms were used in the assay. L1 worms are prepared by plating eggs on a plate without a bacterial feeding layer. The eggs hatch and arrest at the L1 stage. This L1 stage population is then used to create a stock for the experiments. To create an L4 stage stock a small number of worms are taken from an overgrown and starved plate of worms and seeded on a plate with a bacterial feeder layer. A 25 ul aliquot of worms is added to each well in the assay.

To demonstrate that these compounds do not affect nematodes by induction of apoptosis, *Caenorhabditis elegans* mutants defective in the apoptotic pathway, ced-3(n717) and ced-4(N1162) mutants (Ellis H M, Horvitz H R. Genetic control of programmed cell death in the nematode *C. elegans*. 1986 Cell 44:817-829), were evaluated for susceptibility to 10 μg/ml DC5823 on NGM agar plates. No observable phenotypic difference in susceptibility between the wild-type *C. elegans* strain (N2 Bristol) and the ced-3 and ced-4 mutants were observed, including time to mortality.

These data indicate that the claimed structures do not affect apoptosis in either mammalian cells or nematodes.

Example 5

Mouse Acute Toxicity Testing

Acute oral toxicity testing was performed in mice in accordance with test method P203.UDP, as administered by Eurofins/Product Safety Laboratories (Dayton, N.J.). CD-1/Swiss derived albino mice were obtained and group housed in suspended solid bottom caging. The mice were fed rodent chow and filtered tap water was supplied ad libitum. Following acclimation to the laboratory setting, a group of animals was fasted overnight by removing food from the cages. After the fasting period, three female mice were selected based on vitality and initial body weights. The individual compound doses were calculated from these body weights.

The test substance was prepared as a 1% (50 mg/kg) or 5% (500 mg/kg) weight to weight (w/w) mixture in a 0.5% w/w solution of carboxymethylcellulose (CMC) in distilled water. A tissue homogenizer was used to create a homogeneous mixture. A dose of 50 or 500 mg/kg was administered to three healthy mice per dose level by oral intubation using a ball-tipped gavage needle attached to a syringe. After administration, the animals were returned to their cages, and feed was replaced immediately after dosing.

The animals were observed for mortality, signs of gross toxicity and behavioral changes during the first several hours post dosing and at least once daily for up to 14 days. Body weights were recorded prior to initiation and on Days 7 and 14 or a soon as possible after death.

Example 6

Advanced Greenhouse Testing Protocols

Pre-Plant Incorporated Test (PPI)

The PPI test examines the effect of pre-incorporation of compounds in soil and longer aging to simulate in furrow methods of nematicide application in the field. The PPI test exposes compounds to a higher volume of soil and drying which can result in more severe soil binding. Compounds are also aged for longer periods which can lead to more extensive biotic and abiotic degradation further limiting activity.

The chemically treated soil (sandy soil mix) for all treatment days (e.g., 7 days, 14 days, 21 days) treatments is potted into their appropriate pots. On the same day the 7 day treatment pots are seeded. One week later eggs are applied and 14 days after egg application the test is harvested. The 14 day treatments are planted 7 days after the first planting. The 14 day planting and 7 day inoculation happen on the same day. One week later the 14 day treatments are inoculated with eggs. These are harvested 14 days after the inoculation. The 21 day treatments are planted 14 days after the first planting. The 14 day inoculation and 21 day planting are done on the same day. One week later the 21 day plants are inoculated with eggs. The 7 day treatment is harvested the same day as the 21 day inoculation. Fourteen days after inoculation the 21 day plants are harvested.

| Treatment | Planting | Inoculation | Harvest |
|---|---|---|---|
| 7 day | day 0 | day 7 | day 21 |
| 14 day | day 7 | day 14 | day 28 |
| 21 day | day 14 | day 21 | day 35 |

For each compound a stock is prepared using 4 mg material in 4 ml of acetone. The soil is mixed by placing 80 ml of field soil and 320 ml of sand in a plastic bag and mixing well. The formulation for treatment is done by adding 2.13 ml (8 kg/ha rate), 1.06 ml (4 kg/ha rate) or 0.53 ml (2 kg/ha rate) to a vial and raising it with 10 ml in 0.05% X100. Soil is then treated by adding the entire 10 ml to the 400 ml of mix in the bag. The treated soil is immediately mixed well in the sealed bag to distribute the compound evenly. Approximately 95 ml is used to fill each 2-inch square pot up to the top with some soil compression and flattening. For each compound and for the control treatments 4 pots are filled. All pots are watered until moist but with no run-out through the bottom.

The PPI test simulates 8, 4 and 2 kg/ha rates incorporated 15 cm deep in the field and is equivalent to the 2, 1 and 0.5 kg/ha drench application rates in the standard 2-inch pot cucumber greenhouse assay.

Example 9

Seed Treatment Test of Root Knot Nematode on Cucumber Plants and Soybean Cyst Nematode on Soybean Plants For a given concentration the chemical is dissolved in 500 ul of acetone and one gram of cucumber seed (RKN test) or soybean seed (SCN test) is added (e.g., 20 mg active ingredient in 500 ul acetone plus 1 gram of seed). The seed solutions are agitated until all seeds were thoroughly covered with the chemical solution. The acetone is then allowed to evaporate by air drying the seeds. The seeds are planted in 2-inch pots containing sandy soil and then the pots are inoculated with 1000 *Meloidogyne incognita* (RKN) or 1000 *Heterodera glycines* (SCN) eggs per pot three days after planting. Plants are rated for galling 14 days after egg inoculation for RKN or 28 days after egg inoculation for SCN.

Example 10

Description of Synthesis of the Compounds of the Formulas I to XX

The compounds of this invention of the Formulas I to XX may be prepared using methods known to those skilled in the art. Specifically, the compounds of this invention with Formula Ia can be prepared as illustrated by the exemplary reaction in Scheme 1.

Scheme 1: Synthetic scheme to compounds of the Formula Ia

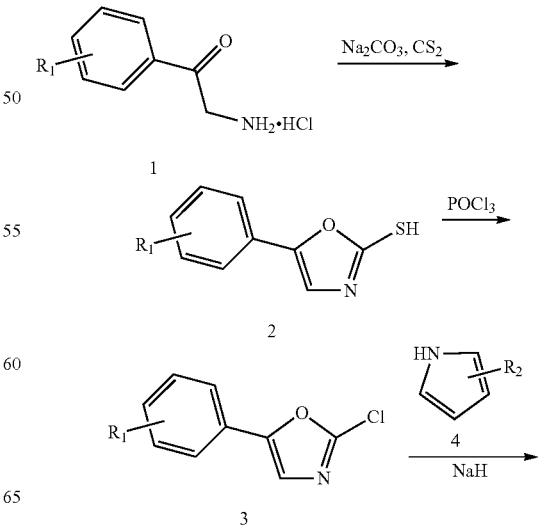

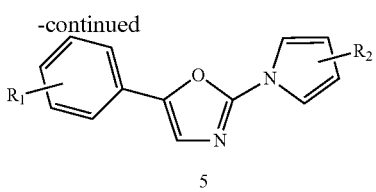

5

The alpha aminoketone 1 is reacted with carbon disulfide in the presence of sodium carbonate in ethanol to yield the corresponding oxazole-2-thiol 2 in good yield with an acceptable purity for the next step. The thiol conversion of the compound 2 to chlorine is accomplished with phosporouschloride (POCl3) in presence of triethylamine at higher temperature. Then, the compound 3 is reacted with the appropriate derivative of pyrrole (after treatment with sodium hydride) at higher temperature to yield the desired 2-pyrrol-5-substituted oxazole analog 5.

Specifically, the compounds of this invention with Formulae IIIa can be prepared as illustrated by the exemplary reaction in Scheme 2.

Scheme 2: Synthetic scheme to compounds of the Formula IIIa

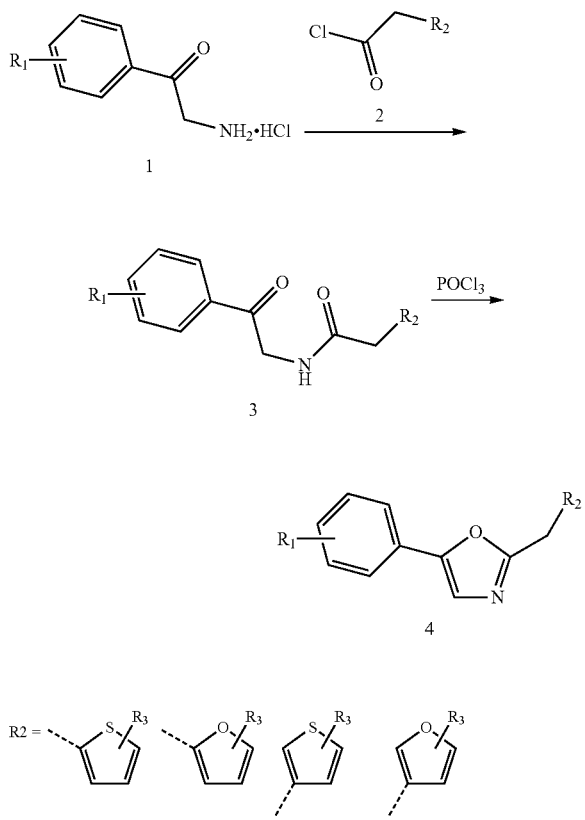

The appropriate alpha amine ketone 1 is reacted with acyl chloride 2 in presence of base to yield the acylaminoketone 3. A cyclization of the linear precursor 3 to corresponding oxazol compound 4 is accomplished with phosporousoxychloride in good yields.

Specifically, the compounds of this invention with Formula VIIIa can be prepared as illustrated by the exemplary reaction in Scheme 3.

Scheme 3: Synthetic scheme to compounds of the Formula VIIIa

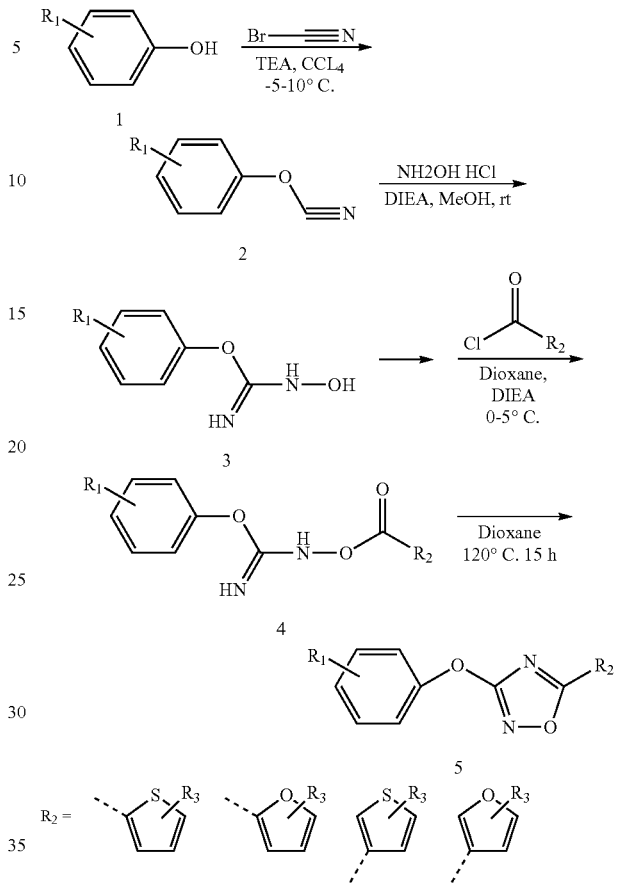

First, cyanogen bromide in tetrachloromethane is reacted with the appropriate phenol analog 1 in the presence of triethylamine to give the corresponding cyanate 2 which in the next step is converted to the corresponding amidoxime 3 by reacting with hydroxylamine in methanol in the presence of DIEA. Then, the amidoxime 3 is reacted with the appropriate analog of acyl chloride to give a linear precursor 4 which after cyclization yields the desired 3,5-disubstituted-1,2,4-oxadiazole 5

Specifically, the compounds of this invention with Formulae IXa can be prepared as illustrated by the exemplary reaction in Scheme 4. The benzonitrile 1 is conerted to the corresponding hydroxyimidate 2 when reacted with hydroxylamine hydrochloride in methanol in the presence of DIEA in methanol at room temperature overnight. Then the benzohydroxyimidate 2 is acylated with an appropriate furan or thiophene acetyl chloride in the presence of DIEA to give a linear precursor 3 which after cyclization yields the desired 3,5-disubstituted 1,2,4-oxadiazole 4.

Scheme 4: Synthetic scheme to compounds of the Formulae IXa

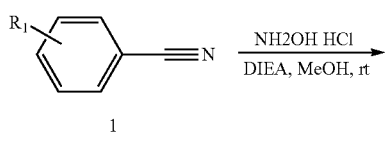

next step the oxathiazoline intermediate 2 is reacted with the appropriate 2-(furanyl) or (thiophenylacetonitrile in toluene under microwave conditions to give the desired 3,5-disubstituted-1,2,4-thiadiazole product 4.

Scheme 6: Synthetic scheme to compounds of the Formula XVa

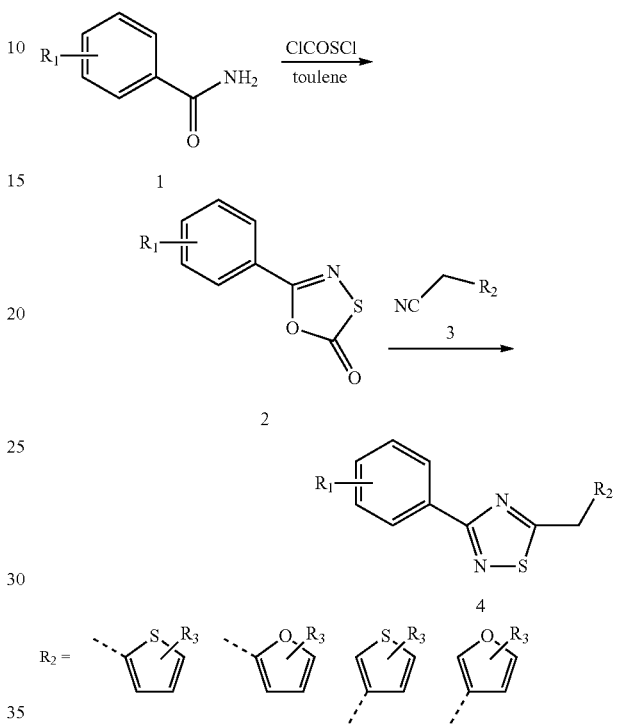

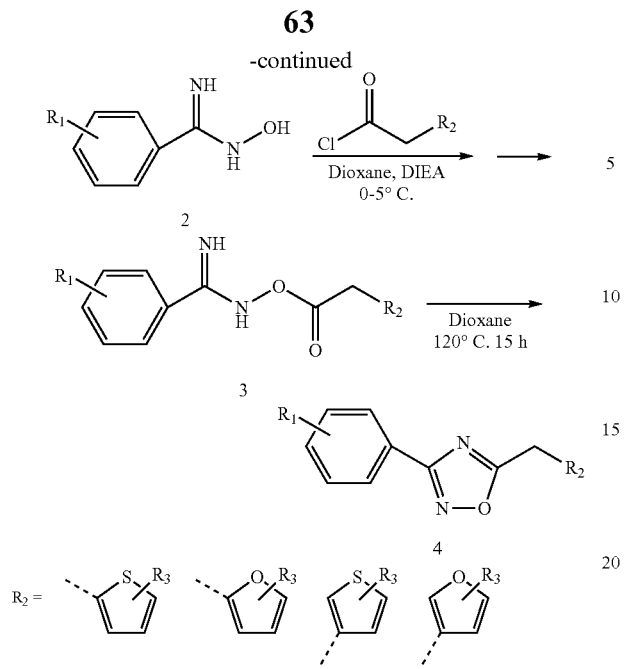

Specifically, the compounds of this invention with Formulae XIIIa can be prepared as illustrated by the exemplary reaction in Scheme 5. The appropriate benzimidamine is reacted with trichloromethyl hypochlorothioite to yield the corresponding 5-chloro-3-substituted-1,2,4-thiadiazole 2. The chlorine displacement of intermediate 2 with the appropriate derivative of pyrrole was accomplished in DMSO to afford the desired 5-pyrrolyl thiadiazole anolog 4

Scheme 5: Synthetic scheme to compounds of the Formula XIIIa

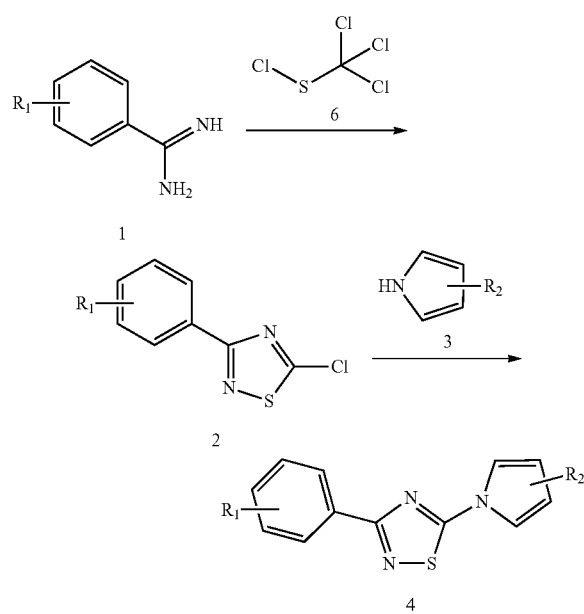

Specifically, the compounds of this invention with Formula XVa can be prepared as illustrated by the exemplary reaction in Scheme 6. The synthesis starts with the reaction of an appropriate benzamide substrate 1 with chlorocarbonylsulfenyl chloride to yield the oxathiazolone compound 2. In the Specifically, the compounds of this invention with Formula XIXb can be prepared as illustrated by the exemplary reaction in Scheme 7.

Scheme 7: Synthetic scheme to compounds of the Formula XIXb

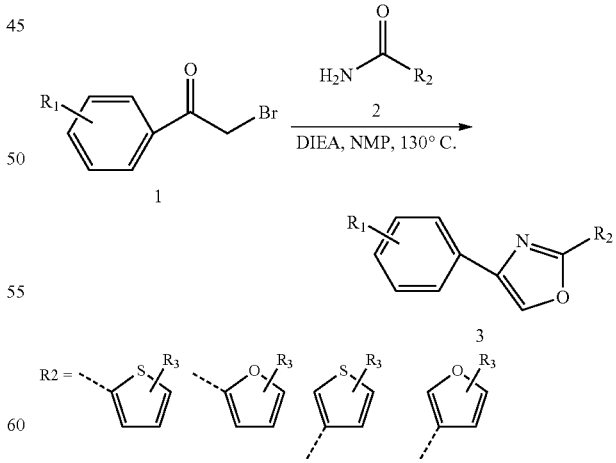

The appropriate alpha-bromoacetophenone 1 is reacted with the corresponding amide analog 2 in N-methylpyrrolidone (NMP) in presence of DIEA at higher temperature to give the desired 2-4-disubstituted oxazol product 3.

Formula Ia Example

5-(4-chlorophenyl)-2-(1H-pyrrol-1-yl)oxazole

The starting 2-amino-1-(4-chlorophenyl)ethanone hydrochloride was prepared according to the following procedure. The 1-(4-chlorophenyl)ethanone (1.0 eq.) was dissolved in glacial acetic acid (1 mL per mmol). To this was added a slurry of pyridinium bromide perbromide (1.03 eq.) in acetic acid (1 mL per mmol). The heterogeneous mixture was stirred for 4 h at ambient temperature. After about 30 min. the mixture turned homogeneous. After pouring into ice-water a yellow precipitate was filtered off and washed with water (2×1 mL per mmol of starting ketone). Drying of the precipitate afforded 2-bromo-1-(4-chlorophenyl)ethanone in ca. 90% yield.

A mixture of 2-bromo-1-(4-chlorophenyl)ethanone (1.0 eq.) and $NaN(CHO)_2$ (1.1 eq.) in acetonitrile (1.5 mL per mmol) was heated to reflux for 4 h at 105° C. ext. temperature. The formed sodium bromide was removed by filtration and the filtrate concentrated in vacuo. The residue was dissolved in ethanol (2.5 mL per mmol) and conc. aq. hydrochloric acid (0.9 mL per mmol) added at ambient temperature. After stirring for 72 h at room temperature the solids were filtered off and washed with ethanol (1×0.5 mL per mmol). Drying of the solids afforded 2-amino-1-(4-chlorophenyl)ethanone hydrochloride in ca. 50% yield that was used in the next step without purification.

2-amino-1-(4-chlorophenyl)ethanone hydrochloride (0.80 g, 3.88 mmol) and carbon disulfide (0.47 mL, 0.59 g, 7.76 mmol) was suspended in ethanol (10 mL). To this was slowly added a solution of sodium carbonate (0.44 g, 4.08 mmol) in water (4 mL) at ambient temperature. After heating to 80° C. ext. temp. for 18 h the cold mixture was filtered. The filtrate was diluted with acetic acid (40 mL) and stirred for 15 min. at room temperature. Evaporation of the solvents in vacuo gave 1.42 g of a crude 5-(4-chlorophenyl)oxazole-2-thiol which was of ca. 61% purity (HPLC-MS) and used as is in the next step. The crude oxazole-2-thiol compound (1.42 g, max. 3.88 mmol) was suspended in phosphorous oxychloride (5 mL). To this was added dropwise triethyl amine (1.15 mL, 0.84 mg, 8.27 mmol) and the mixture heated to 105° C. ext. temperature for 4 h. The reaction mixture was poured into water (50 mL) and extracted with ethyl acetate (3×40 mL). The combined organic layers were washed with aq. sat. bicarbonate (100 mL) and water (50 mL). Drying (sodium sulfate) and concentration in vacuo yielded crude product (615 mg), which was purified by column chromatography ($SiO_2$, 5-40% ethyl acetate in heptanes) to give pure 2-chloro-5-(4-chlorophenyl)oxazole (105 mg, 0.49 mmol, 13%, purity 96% HPLC-MS).

In the next step, pyrrole (2 mL) was treated with sodium hydride (10 mg, 0.22 mmol, 55% wetted with mineral oil), then 75-(4-chlorophenyl)-2-(1H-pyrrol-1-yl)oxazole (45 mg, 0.21 ml) was added. The mixture was heated to 60° C. ext. temperature for 1 h, 85° C. for 6 h and 100° C. for 6 h. More sodium hydride (10 mg, 0.22 mmol, 55% wetted with mineral oil) was added and the reaction mixture heated to 120° C. external temperature for 6 h. Analysis (HPLC-MS) showed the starting material to be consumed. The mixture was evaporated to dryness in vacuo and partitioned between aq. sat. ammonium chloride and ethyl acetate. Extraction of the water layer with ethyl acetate (3×50 mL) and evaporation of the combined organic layers in vacuo gave crude product (80 mg), which was purified by column chromatography ($SiO_2$, 0-20% ethyl acetate in heptanes) to afford pure 5-(4-chlorophenyl)-2-(1H-pyrrol-1-yl)oxazole (18 mg, 72.4 mol, yield 35%, purity 98.6% (HPLC-MS). LC-MS [M+H] 245 (C13H9ClN2O+H, requires 245.04). $^1$H-NMR spectra is in accordance with the chemical structure.

Formula IIIa Example

5-(4-chlorophenyl)-2-(thiophen-2-ylmethyl)oxazole

A mixture of amine.HCl 1 (1.0 g, 4.85 mmol), 2-thiophen-2yl-acetyl chloride (0.80 g, 5.0 mmol) and $NaHCO_3$ (3.0 g, 36 mmol) in EtOAc (20 mL) and water (20 mL) was vigorously stirred for 16 h. After dilution with water (50 mL) the layers were separated. The water layer was again extracted with EtOAc. The combined organic layers were washed with brine, dried and concentrated to an orange solid, 1.0 g. After trituration with MTBE, acylamide 3 was obtained as yellow solid, 0.9 g (yield 64%)

A mixture of acylamide 3 (0.76 g, 2.6 mmol) and $POCl_3$ (4.5 g, 29 mmol) was heated to reflux for 2 h. After cooling to r.t the mixture was concentrated in vacuo. The residue was taken in $CH_2Cl_2$ and washed with saturated aqueous $NaHCO_3$, dried and concentrated to a brown oil, 600 mg. Column chromatography on $SiO_2$ (elution with Heptane/EtOAc 2/1) gave pure 5-(4-chlorophenyl)-2-(thiophen-2-yl-methyl)oxazole as an oil that solidified on standing, 300 mg, yield 42%. HPLC purity 99.6% (254 nm); LC-MS [M+H] 276 (M+1) (C14H10ClNOS+H, requires 276.02). $^1$H-NMR spectra is in accordance with the chemical structure

Formula VIIIa Example

3-(4-Chloro-phenoxy)-5-furan-2-yl-[1,2,4]oxadiazole

The solution of cyanogen bromide (222 mg, 2.1 mmol, 1.05 eq) in tetrachloromethane (1.5 mL) was cooled down to −5° C. A solution of 4-chlorophenol (256 mg, 2 mmol, 1 eq) in of tetrachloromethane (1.5 mL) was added in one portion to the mixture. The resulting mixture was stirred vigorously while TEA (0.28 mL, 2 mmol, 1 eq) was added dropwise. After an additional 15 min stirring reaction was completed (monitored by LCMS). Reaction mixture was diluted with water and product was extracted with $CH_2Cl_2$ (2×50 mL). Organic phases were combined, washed with brine (2×50 mL), dried over anh. $Na_2SO_4$ and evaporated in vacuo to provide desired cyanate (200 mg, 65%), which was used in the next step of synthesis without further purification.

To the solution of 1-chloro-4-cyanatobenzene (200 mg, 1.3 mmol, 1 eq) in MeOH (2 mL) was added NH2OH hydrochloride (160 mg, 2.3 mmol, 1.8 eq) followed by DIEA (0.45 mL, 2.6 mmol, 2 eq) at 5° C. After 15 min stirring at room temperature reaction was completed (by LCMS). Reaction mixture was diluted with 2M HCl (30 mL) and extracted with EtOAc (2×30 mL). The combined aqueous layers were adjusted to pH 8 with 2M sodium hydroxide and product was extracted with EtOAc (2×40 mL) and washed with brine (2×40 mL). Organic layer was dried over anhydrous $Na_2SO_4$, and concentrated in vacuo to give target 4-chlorophenyl hydroxycarbamimidate in a yield of 70%. Compound was used in the next step of synthesis without further purification.

To the mixture of 4-chlorophenyl hydroxycarbamimidate (0.5 mmol. 1 eq) and DIEA (1.25 mmol, 2.5 eq) in dioxane was added dropwise furan-2-carbonyl chloride (0.53 mmol, 1.05 eq) at 0-5° C. The mixture was allowed to warm to room temperature and then stirred for 0.5-1 h or until complete as determined by LC-MS analysis of the reaction mixture. The cyclodehydration reaction was run at reflux (115-120° C.)

overnight. The mixture was cooled down and solvent was removed in vacuo. The resulting residue was purified by HPLC purification to provide desired 3-(4-Chloro-phenoxy)-5-furan-2-yl-[1,2,4]oxadiazole in a yield of 50% and purity of 99.9%. LC-MS [M+H] 263.3 (C12H7ClN2O3+H, requires 263.65). $^1$H NMR (DMSO-d$_6$) δ 8.17 (d, 1H, J=1.75), 7.63 (d, 1H, J=3.5), 7.55 (d, 2H, J=8.8), 7.46 (d, 2H, J=8.8), 6.87 (m, 1H).

Formula IXa Example 3-(4-Chloro-phenyl)-5-furan-2-ylmethyl-[1,2,4]oxadiazole

To the solution of 4-chlorobenzonitrile (5 mmol, 1 eq) in EtOH (6 mL) was added 50% aqueous solution of hydroxylamine (7.5 mmol, 1.5 eq). Reaction mixture was heated at 110° C. overnight (LCMS indicated reaction was completed). After cooling to room temperature, the reaction was poured into 2M hydrochloric acid (100 mL) and extracted with EtOAc (2×100 mL). The combined aqueous layers were adjusted to pH 8 with 2M sodium hydroxide. Product was extracted with EtOAc (2×100 mL). Organic extract was washed with brine (2×80 mL), dried over anhydrous Na$_2$SO$_4$ and concentrated in vacuo to give pure target amidoxime as a white solid.

To the mixture of 2-furylacetic acid (0.5 mmol, 1 eq), DIEA (1 mmol, 2 eq) and 1,1'-carbonyldiimidazole (0.6 mmol, 1.2 eq) in dioxane was added 4-chloro-N-hydroxybenzimidamide (0.5 mmol, 1 eq) at room temperature. After 30 min stirring at room temperature the mixture was heated at 115-120° C. overnight. The mixture was cooled down and solvent was removed in vacuo. The residue was dissolved in DMSO (1-0.5 mL) and purified by HPLC purification to give target 3-(4-Chloro-phenyl)-5-furan-2-ylmethyl-[1,2,4]oxadiazole as a white solid in a yield of 62% and HPLC purity of 99.7%. LC-MS [M+H] 261.4 (C13H9ClN2O2+H, requires 261.68). $^1$H NMR (DMSO-d$_6$) δ 8.01 (d, 2H, J=8.5), 7.64 (d, 2H, J=8.5), 7.62 (s, 1H), 6.46 (s, 2H), 4.58 (s, 2H).

Formulae XIIIa Example 3-(4-chlorophenyl)-5-(1H-pyrrol-1-yl)-1,2,4-thiadiazole

To a suspension of 4-chlorobenzimidamide (0.5 g, 2.62 mmol) in DCM (10 mL) was added trichloromethyl hypochlorothioite (0.30 mL, 0.54 g, 2.74 mmol). The mixture was cooled to 0° C. ext. temperature, aq. 6N NaOH (3 mL) added and the solution stirred for 30 min. After dilution with water (25 mL) and extraction of the water layer with DCM (2×50 mL) the combined organic layers were dried with sodium sulfate and concentrated in vacuo to afford crude 5-chloro-3-(4-chlorophenyl)-1,2,4-thiadiazole (630 mg). The purification by column chromatography (SiO$_2$, 0-10% ethyl acetate in heptanes) gave 319 mg (1.38 mmol) of the pure product in a yield of 53%.

The 5-chloro-1,2,4-thiadiazole compound (102 mg, 0.445 mmol) was dissolved in DMSO (2 mL) and pyrrol (300 mg, 2.22 mmol) added at room temperature. The mixture was heated for 18 h to 55° C. ext. temperature, however no conversion was found (sample tested by $^1$H-NMR). Sodium hydride (55% wetted with mineral oil, 20 mg, 0.467 mmol) was added and the mixture heated to 80° C. ext. temperature for 5 h. As the conversion was not complete (sample tested by $^1$H-NMR) the mixture was heated to 100° C. ext. temperature for 6 h. The reaction mixture was poured into water (10 mL) and crude product isolated by filtration. The purification by column chromatography (SiO$_2$, 0-10% ethyl acetate inheptanes) afforded 3-(4-chlorophenyl)-5-(1H-pyrrol-1-yl)-1,2,4-thiadiazole (52 mg, 0.199 mmol, 45%), which was 98% pure (HPLC 254 nm). $^1$H-NMR spectra is in accordance with the chemical structure.

Formula XVa Example 3-(4-chlorophenyl)-5-(thiophen-2-ylmethyl)-1,2,4-thiadiazole A mechanically stirred mixture of 4-chlorobenzamide (20.23 g, 130 mmol), toluene (150 mL), and chlorocarbonylsulfenylchloride (19 g, 145 mmol) was heated to reflux for 3 h. After cooling to r.t. the mixture was concentrated in vacuo to give a yellow solid foam, 27.65 g (100%). H-NMR showed that this was almost pure oxathiazolone compound that was used as is in the next step.

A mixture of oxathiazolone 2 (0.25 g, 1.17 mmol) and 2-thiopheneacetonitrile (3.5 g, 27 mmol) was heated in the microwave at 190° C. for 20 min. Excess furonitrile and volatile byproducts were removed in vacuo (170° C., 2 mbar). The residual brown oil (300 mg) was purified by column chromatography in SiO$_2$ (Heptane-EtOAc 3-1) to give 30 mg of impure product. Further purification by preparative HPLC gave 3-(4-chlorophenyl)-5-(thiophen-2-ylmethyl)-1,2,4-thiadiazole, as brown solid, 7 mg (yield 2%) and HPLC purity of 95% (254 nm). HPLC-MS (M+1)=293(C13H9ClN2S2+H, requires 293). 1H-NMR spectra is in accordance with the chemical structure.

Formula XIXb Example 4-(2,4-Dichloro-phenyl)-2-furan-2-yl-oxazole

To the solution of furan-2-carboxamide (56 mg, 0.5 mmol. 1 eq) and DIEA (0.13 mL, 0.75 mmo, 1.5 eq) in NMP (1 mL) was added 2-bromo-1-(2,4-dichlorophenyl)ethanone (0.6 mmol, 1.2 eq). Reaction mixture was heated at 130° C. for 15 h. The mixture was cooled down, diluted with 1 M HCl (30 mL) and extracted with EtOAc (40 mL). The organic layer was washed with 1 M HCl (30 mL), 5% solution of NaHCO$_3$ (30 mL), brine (2×40 mL), dried over anhydrous Na$_2$SO$_4$, and concentrated in vacuo. The resulting residue was purified by HPLC purification to provide desired 4-(2,4-Dichloro-phenyl)-2-furan-2-yl-oxazole in a yield of 55% and HPLC 99.9% purity. LC-MS [M+H]–280.4 (C13H7Cl2NO2+H, requires 281.11). $^1$H NMR (DMSO-d$_6$) δ 8.84 (s, 1H), 8.13 (d, 1H, J=8.5), 8.01 (s, 1H), 7.78 (s, 1H), 7.58 (d, 1H, J=8.5), 7.29 (d, 1H, J=3.5), 6.77 (m, 1H).

What is claimed is:
1. A compound of Formula VIII or a salt thereof,

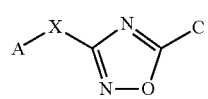

Formula VIII wherein,
A is an optionally singly or independently multiply substituted aryl, an optionally singly or independently multiply substituted arylalkyl, an optionally singly or independently multiply substituted heteroaryl or an optionally singly or independently multiply substituted heteroarylalkyl wherein the substituents are selected from the group consisting of halo, $C_1$-$C_6$ haloalkyl, $C_6$-$C_{10}$ aryl, $C_4$-$C_7$ cycloalkyl, $C_2$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$) alkenyl, $C_6$-$C_{10}$ aryl($C_2$-$C_6$) alkynyl, $C_1$-$C_6$ hydroxyalkyl, amino, ureido, cyano, $C_1$-$C_6$ acylamino, hydroxy, thiol, $C_1$-$C_6$ acyloxy, azido, $C_1$-$C_6$ alkoxy and carboxy, and C(H)O;

C is a heteroaryl selected from the group consisting of furanyl, oxazolyl, or isoxazolyl, each of which can be optionally singly or independently multiply substituted with one or more substituents selected from the group consisting of fluorine, chlorine, $CH_3$ and $OCF_3$; and X is O or S.

2. The compound of claim 1 wherein A is an optionally singly or independently multiply substituted heteroaryl.

3. The compound of claim 2 wherein A is selected from the group consisting of pyridyl, pyrazyl, oxazolyl and isoxazolyl, each of which can be optionally singly or independently multiply substituted, wherein the substituents are selected from the group consisting of halo, $C_1$-$C_6$ haloalkyl, $C_6$-$C_{10}$ aryl, $C_4$-$C_7$ cycloalkyl, $C_2$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$) alkenyl, $C_6$-$C_{10}$ aryl($C_2$-$C_6$)alkynyl, $C_1$-$C_6$ hydroxyalkyl, amino, ureido, cyano, $C_1$-$C_6$ acylamino, hydroxy, thiol, $C_1$-$C_6$ acyloxy, azido, $C_1$-$C_6$ alkoxy and carboxy, and C(H)O.

4. The compound of claim 1 of Formula VIIIa or a salt thereof

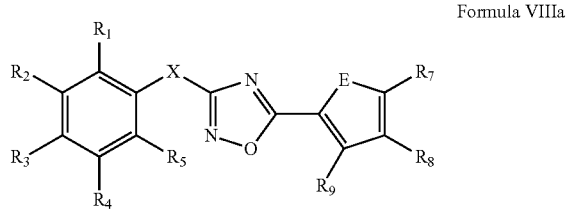

Formula VIIIa wherein,
$R_1$ and $R_5$ are independently selected from the group consisting of hydrogen, $CH_3$, $OCH_3$, F, Cl, Br, $CF_3$, and $OCF_3$;
$R_2$ and $R_4$ are independently selected from the group consisting of hydrogen, F, Cl, Br, $CH_3$, and $CF_3$;
$R_3$ is selected from the group consisting of hydrogen, $CH_3$, $CF_3$, F, Cl, Br, $OCF_3$, $OCH_3$, CN, and C(H)O;
$R_7$, $R_8$ and $R_9$ are independently selected from the group consisting of hydrogen, F, Cl, $CH_3$, and $OCF_3$;
E is O; and
X is O or S.

5. The compound of claim 1 of formula VIIIb or a salt thereof

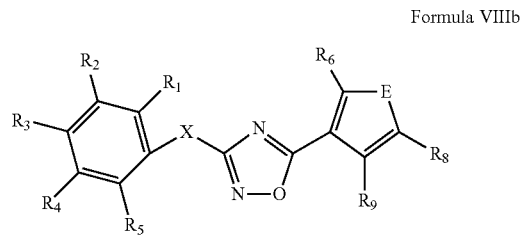

Formula VIIIb wherein,
$R_1$ and $R_5$ are independently selected from the group consisting of hydrogen, $CH_3$, $OCH_3$, F, Cl, Br, $CF_3$, and $OCF_3$;
$R_2$ and $R_4$ are independently selected from the group consisting of hydrogen, F, Cl, Br, $CH_3$, and $CF_3$;
$R_3$ is selected from the group consisting of hydrogen, $CH_3$, $CF_3$, F, Cl, Br, $OCF_3$, $OCH_3$, CN, and C(H)O;
$R_6$, $R_8$ and $R_9$ are independently selected from the group consisting of hydrogen, F, Cl, $CH_3$, and $OCF_3$;
E is O; and
X is O or S.

6. A compound of Formula IXa or a salt thereof,

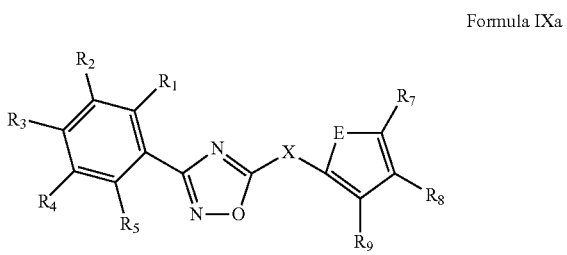

Formula IXa wherein,
$R_1$ and $R_5$ are independently selected from the group consisting of hydrogen, $CH_3$, $OCH_3$, F, Cl, Br, $CF_3$, and $OCF_3$;
$R_2$ and $R_4$ are independently selected from the group consisting of hydrogen, F, Cl, Br, $CH_3$, and $CF_3$;
$R_3$ is selected from the group consisting of hydrogen, $CH_3$, $CF_3$, F, Cl, Br, $OCF_3$, $OCH_3$, CN, and C(H)O;
$R_7$, $R_8$ and $R_9$ are independently selected from the group consisting of hydrogen, F, Cl, $CH_3$, and $OCF_3$;
E is O or S; and
X is $CH_2$, O or S.

7. A method for control of unwanted nematodes, the method comprising administering to mammals, birds, or their food, plants, seeds or soil a composition comprising an effective amount of a compound of Formula VIII or a salt thereof,

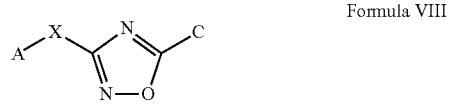

Formula VIII wherein,
A is an optionally singly or independently multiply substituted aryl, an optionally singly or independently multiply substituted arylalkyl, an optionally singly or independently multiply substituted heteroaryl or an optionally singly or independently multiply substituted heteroarylalkyl wherein the substituents are selected from the group consisting of halo, $C_1$-$C_6$ haloalkyl, $C_6$-$C_{10}$ aryl, $C_4$-$C_7$ cycloalkyl, $C_2$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$) alkenyl, $C_6$-$C_{10}$ aryl($C_2$-$C_6$) alkynyl, $C_1$-$C_6$ hydroxyalkyl, amino, ureido, cyano, $C_1$-$C_6$ acylamino, hydroxy, thiol, $C_1$-$C_6$ acyloxy, azido, $C_1$-$C_6$ alkoxy and carboxy, and C(H)O;

C is an optionally singly or independently multiply substituted heteroaryl wherein the substituents are selected from the group consisting of fluorine, chlorine, $CH_3$ and $OCF_3$; and X is O or S.

8. The method of claim 7 wherein the composition comprises a surfactant.

9. The method of claim 7 wherein the composition comprises a co-solvent.

10. The method of claim 7 wherein the composition includes one or more of: a fungicide, a herbicide, and a pesticide.

11. A composition comprising the compound of claim 1 in an aqueous carrier.

12. The composition of claim 11 wherein the composition comprises a surfactant.

13. The composition of claim 11 wherein the composition comprises a co-solvent.

14. A method for control of unwanted nematodes, the method comprising administering to mammals, birds, or their food, plants, seeds or soil a composition comprising an effective amount of a compound of claim 6.

15. The method of claim 14 wherein the composition comprises a surfactant.

16. The method of claim 14 wherein the composition comprises a co-solvent.

17. The method of claim 14 wherein the composition includes one or more of: a fungicide, a herbicide, and a pesticide.

18. A composition comprising the compound of claim 6 in an aqueous carrier.

19. The composition of claim 18 wherein the composition comprises a surfactant.

20. The composition of claim 18 wherein the composition comprises a co-solvent.

21. The compound of claim 1 wherein the compound is 3-(4-chlorophenoxy)-5-(furan-2-yl)-1,2,4-oxadiazole.

22. The method of claim 7 wherein the compound is 3-(4-chlorophenoxy)-5-(furan-2-yl)-1,2,4-oxadiazole.

23. The composition of claim 11 wherein the compound is 3-(4-chlorophenoxy)-5-(furan-2-yl)-1,2,4-oxadiazole.

24. The compound of claim 1 wherein the compound is 3-(3-chlorophenoxy)-5-(furan-2-yl)-1,2,4-oxadiazole.

25. The method of claim 7 wherein the compound is 3-(3-chlorophenoxy)-5-(furan-2-yl)-1,2,4-oxadiazole.

26. The composition of claim 11 wherein the compound is 3-(3-chlorophenoxy)-5-(furan-2-yl)-1,2,4-oxadiazole.

27. The compound of claim 6 wherein the compound is 3-(4-chlorophenyl)-5-(furan-2-ylmethyl)-1,2,4-oxadiazole.

28. The method of claim 14 wherein the compound is 3-(4-chlorophenyl)-5-(furan-2-ylmethyl)-1,2,4-oxadiazole.

29. The composition of claim 18 wherein the compound is 3-(4-chlorophenyl)-5-(furan-2-ylmethyl)-1,2,4-oxadiazole.

30. The compound of claim 6 wherein the compound is 3-(3-chlorophenyl)-5-(furan-2-ylmethyl)-1,2,4-oxadiazole.

31. The method of claim 14 wherein the compound is 3-(3-chlorophenyl)-5-(furan-2-ylmethyl)-1,2,4-oxadiazole.

32. The composition of claim 18 wherein the compound is 3-(3-chlorophenyl)-5-(furan-2-ylmethyl)-1,2,4-oxadiazole.

* * * * *